(12) United States Patent
Kounovsky-Shafer et al.

(10) Patent No.: US 11,668,631 B2
(45) Date of Patent: Jun. 6, 2023

(54) DEVICES AND METHODS FOR ELUTING AND CONCENTRATING LARGE DNA MOLECULES

(71) Applicant: Board of Regents of the University of Nebraska, Lincoln, NE (US)

(72) Inventors: Kristy Leigh Kounovsky-Shafer, Kearney, NE (US); Cody Dean Masters, Kearney, NE (US); Jocelyn Dolphin, Blair, NE (US); April Vonderfecht, Deshler, NE (US)

(73) Assignee: NUtech Ventures, Lincoln, NE (US)

( * ) Notice: Subject to any disclaimer, the term of this patent is extended or adjusted under 35 U.S.C. 154(b) by 669 days.

(21) Appl. No.: 16/592,695

(22) Filed: Oct. 3, 2019

(65) Prior Publication Data

US 2020/0110009 A1     Apr. 9, 2020

Related U.S. Application Data

(60) Provisional application No. 62/740,921, filed on Oct. 3, 2018.

(51) Int. Cl.
*B01L 3/00* (2006.01)
*G01N 1/40* (2006.01)
(Continued)

(52) U.S. Cl.
CPC ........... *G01N 1/4005* (2013.01); *B01L 3/508* (2013.01); *C12N 15/1017* (2013.01);
(Continued)

(58) Field of Classification Search
CPC ........... G01N 1/4005; G01N 27/44747; G01N 2001/4016; G01N 2001/4038;
(Continued)

(56) References Cited

U.S. PATENT DOCUMENTS

| 6,203,680 B1* | 3/2001 | Cole | ............... G01N 27/44747 |
| | | | 204/462 |
| 2010/0126862 A1* | 5/2010 | Sabin | .................. G01N 27/447 |
| | | | 204/627 |

OTHER PUBLICATIONS

Wang, Yu-Ker, and David C. Schwartz. "Chopped inserts: a convenient alternative to agarose/DNA inserts or beads." Nucleic acids research 21.10 (1993): 2528. (Year: 1993).*

(Continued)

*Primary Examiner* — Jennifer Wecker
*Assistant Examiner* — Oyeleye Alexander Alabi
(74) *Attorney, Agent, or Firm* — Fish & Richardson P.C.

(57) ABSTRACT

This disclosure relates to mesofluidic devices and methods for eluting and concentrating a plurality of nucleic acid molecules. The mesofluidic device includes a device frame having a bottom surface upon which is defined a first reservoir and the second reservoir. The first reservoir includes a first electrode, and the second reservoir includes a second electrode. The first and second electrodes are configured for electrical connection. The mesofluidic device includes an elongated channel extending between the first reservoir and the second reservoir. The mesofluidic device includes a first slot having a first slot width. The first slot is configured to receive an insert. The first slot intersects the elongated channel. The mesofluidic device includes a second slot having a second slot width. The second slot is configured to receive a separation material having a first porosity. The second slot intersects the elongated channel.

20 Claims, 15 Drawing Sheets

(51) Int. Cl.
*C12N 15/10* (2006.01)
*G01N 27/447* (2006.01)

(52) U.S. Cl.
CPC ... *G01N 27/44747* (2013.01); *B01L 2300/0645* (2013.01); *B01L 2300/0681* (2013.01); *B01L 2300/12* (2013.01); *G01N 2001/4016* (2013.01); *G01N 2001/4038* (2013.01); *G01N 2001/4088* (2013.01)

(58) Field of Classification Search
CPC .......... G01N 2001/4088; G01N 27/447; B01L 3/508; B01L 2300/0645; B01L 2300/0681; B01L 2300/12; B01L 3/502707; B01L 3/50273; B01L 3/502761; B01L 2200/0668; B01L 2300/0858; B01L 2400/0421; C12N 15/1017
See application file for complete search history.

(56) References Cited

OTHER PUBLICATIONS

Bordelon et al., "A Magnetic Bead-Based Method for Concentrating DNA from Human Urine for Downstream Detection," PloS one, 2013, 8(7):e68369.
Chen et al., "A comprehensive survey of copy number variation in 18 diverse pig populations and identification of candidate copy number variable genes associated with complex traits," BMC Genomics, 2012, 13:733.
Conrad et al., "Origins and functional impact of copy number variation in the human genome," Nature, 2010, 464(7289):704-712.
Dimalanta et al., "A microfluidic system for large DNA molecule arrays," Anal Chem, 2004, 76:5293-5301.
Freeman et al., "Copy number variation: New insights in genome diversity," Genome Res, 2006, 16:949-961.
Garvin et al., "Purifying and concentrating genomic DNA from mock forensic samples using Millipore Amicon filtersm" J Forensic Sci, 2013, 58 Suppl I:S173-175.
Genomes Project et al., "A global reference for human genetic variation," Nature 2015, 526(7571):68-74.
Gupta et al., "Optical mapping and nanocoding approaches to whole-genome analysis," Microfluidics and Nanofluidics 2016, 20:1-14.
Gupta et al., "Single-molecule analysis reveals widespread structural variation in multiple myeloma," Proc Natl Acad Sci, 2015, 112(25):7689-7694.
Herschleb et al., "Pulsed-field gell electrophoresis," Nat Protoc 2007, 2:677-684.
Hudlow et al., "The NucleoSpin® DNA Clean-up XS kit for the concentration and purification of genomic DNA extracts: an alternative to microdialysis filtration," Forensic Science Int Genet, 2011, 5(3):226-230.
Jo et al., "A single-molecule barcoding system using nanoslits for DNA analysis" Methods n Molecular Biology, 2009, 29-42.
Kim et al., "Nanochannel confinement: DNA stretch approaching full contour length," Lab Chip, 2011, 11(10):1721-1729.
Kounovsky-Shafer et al., "Electrostatic confinement and manipulation of DNA molecules for genome analysis," Proc Natl Acad Sci USA, 2017, 114, 13400-13405.
Kounovsky-Shafer et al., "Presentation of Large DNA Molecules for Analysis as Nanoconfined Dumbbells," Macromolecules 2013, 46(20):8356-8368.
Lallman et al., "Determination of electroosmotic and electrophoretic mobility of DNA and dyes in low ionic strength solutions," Electrophoresis 2018, 39:862-868.
Maschmann et al., "Determination of restriction enzyme activity when cutting DNA labeled with the TOTO Dye family," Nucleosides Nucleotides Nucleic Acids, 2017, 36(6):406-417.
Masters et al., "Developed 3D printers mesofluidic devices to elute and concentrate DNA," Univeristy of Nebraska, 16 pages.
Meng et al., "Inhibition of restriction endonuclease activity by DNA binding fluorochromes," J. Biomol. Struct. Dyn., 1996, 13(6):945-951.
Rueden et al., "ImageJ2: ImageJ for the next generation of scientific image data," BMC Bioinformatics 2017, 18(1):529.
Schwartz et al. "Separation of yeast chromosome-sized DNAs by pulsed field gradient gel electrophoresis," Cell, 1984, 37:67-75.
Stefansson et al., "CNVs conferring risk of autism or schizophrenia affect cognition in controls," Nature, 2014, 505:361-366.
Stellwagen, "Electrophoresis of DNA in agarose gels, polyacrylamide gels and in free solution," Electrophoresis, 2009, 30 Suppl I:S188-195.
Teague et al., "High-resolution human genome structure by single-molecule analysis," Proc Natl Acad Sci U S A, 2010, 107(24):10848-10853.
Wang et al., "Copy number variation at the GL7 locus contributes to grain size diversity in rice," Nat Genet, 2015, 47(8):944-948.

* cited by examiner

DEVICES AND METHODS FOR ELUTING AND CONCENTRATING LARGE DNA MOLECULES

CROSS-REFERENCE TO RELATED APPLICATIONS

This application claims priority to U.S. Provisional Patent Application No. 62/740,921, filed Oct. 3, 2018. The content this application is incorporated herein by reference in its entirety.

STATEMENT OF FEDERALLY SPONSORED RESEARCH

This invention was made with government support under P20 GM103427 awarded by the National Institutes of Health. The government has certain rights in the invention.

BACKGROUND

Structural variation in the human genome accounts for a larger number of bases varied than single nucleotide polymorphisms [1, 2] and has been linked to various diseases [3-5]. These variations are at least 1 kb in size or greater [6], but larger structural variations (>50 kb) are difficult to determine due to their large size compared to single nucleotide polymorphisms or small insertion and deletions. Physical mapping platforms (Optical Mapping [7-9] and Nanocoding [10-13]) are able to span these large structural variations (5 kb—hundreds of kilobases in size to megabase in size). However, in order to span extremely large insertions or inversions, molecules need to be long enough to span the variation with enough information on each side to allow for alignment.

In Nanocoding, fluorescently labelled DNA with sequence-specific information highlighted with fluorescently labelled nucleotides are driven into nanoslits with an electric field and then the electric field is turned off to form a DNA dumbbell. A dumbbell occurs when the molecule traverses the nanoslit, electric field is turned off, so both ends of the molecule reside in opposing microchannels [10, 12-14]. In order to analyze large genomes, a population of large DNA is required to analyze the genome and find large structural variations in the genome. In order to discern large structural variations, molecules that span the variation with enough unique information on either end are required to understand complex genomes, such as cancer. With Nanocoding's unique method of presentation, which allows DNA to be uniformly stretched at specific locations within the device (nanoslits), large molecules are required with a minimum size to form a dumbbell in order to present a complete genomic scaffold to determine structural variations.

Large DNA molecules, needed to span large structural variations, are fragile and during routine molecular biology manipulations will break. Therefore, improvements in DNA isolation techniques and devices are continually sought.

SUMMARY

The mesofluidic devices and methods for eluting and concentrating a plurality of nucleic acid molecules can be implemented to concentrate nucleic acid molecules of a variety of sizes for use in, for example, whole genome analysis systems. In this section, examples of such mesofluidic devices and methods are described. However, it should be understood that in general, the various steps and techniques discussed herein can be performed using a variety of different designs, sizes, and geometries of mesofluidic devices, not all of which are expressly set forth.

Various embodiments of the present disclosure relate to mesofluidic devices and related methods of using the mesofluidic devices, preferably intended for use in eluting and concentrating a plurality of nucleic acid molecules of a length exceeding about 1 kilobase (kb). In some embodiments, a distinct advantage of the control slides provided herein is that it can be used to elute and concentrate large DNA molecules. To understand structural variation for personal genomics, an extensive ensemble of large DNA molecules is required to span large structural variations. Nanocoding, a whole-genome analysis platform, can analyze large DNA molecules for the construction of physical restriction maps of entire genomes.

However, handling of large DNA is difficult and a system is needed to concentrate large DNA molecules, while keeping the molecules intact. Insert technology was developed to protect large DNA molecules during routine cell lysis and molecular biology techniques. For example, Schwartz et al. developed insert technology to protect DNA during cell lysis and other routine molecular biology manipulations when they developed pulsed-field gel electrophoresis [15, 16].

Getting large DNA out of the insert and into solution is difficult due to the fragility of the molecules and Nanocoding requires a very low ionic strength solution to form fully stretched DNA dumbbells. Therefore, a system is required to elute and then concentrate large DNA without breaking them for Nanocoding or other sequencing platforms. In sum, eluting and concentrating DNA molecules has been difficult in the past.

Amicon filters and NucleoSpin gDNA are able to readily concentrate small DNA and are the go-to method of concentrating PCR products, proteins, and plasmids, but are limited to smaller DNA sizes [17, 18]. The filters are optimized for PCR products and plasmids, which are smaller than the size required for Nanocoding. Other methods use magnetic particles to enrich DNA concentration (75, 100, 140 bp), but would be difficult to scale up and implement this system for extremely large DNA molecules needed for Nanocoding or other sequencing platforms aiming for molecules that are hundreds of kilobase pairs [19].

Utilizing 3D printed mesofluidic devices, a system is provided herein to elute and concentrate lambda DNA molecules at the interface between a solution and a polyacrylamide gel roadblock. The matrix allowed buffer solution to move through the pores in the matrix; however, it slowed down the progression of DNA in the matrix, since the molecules were so large and the pore size was small. Using fluorescence intensity of the insert, 84% of DNA was eluted from the insert and 45% of DNA was recovered in solution from the eluted DNA. DNA recovered was digested with a restriction enzyme to determine that the DNA molecules remained full length during the elution and concentration of DNA.

In one aspect, provided herein are mesofluidic devices for eluting and concentrating a plurality of nucleic acid molecules, the mesofluidic devices include a device frame having a bottom surface upon which is defined a first reservoir comprising a first electrode, a second reservoir comprising a second electrode, the first and second electrodes configured for electrical connection, and an elongated channel extending between the first reservoir and the second reservoir, the elongated channel having a channel width; a first slot having a first slot width, the first slot configured to receive an insert, wherein the first slot intersects the elongated channel; and a second slot having a second slot width, the second slot configured to receive a separation material having a first porosity wherein the second slot intersects the elongated channel, wherein the first slot width and the second slot with width are greater than the channel width.

In some embodiments, the plurality of nucleic acid molecules includes deoxyribonucleic acid (DNA) molecules. In some embodiments, the mesofluidic devices provided herein further include an electrical wire electrically connecting the first and second electrodes to a power supply. In some embodiments, the first slot defines an insert region. In some embodiments, the insert comprises the plurality of nucleic acid molecules and agarose. In some embodiments, the separation material is a gel, a filter, or a physical barrier. In some embodiments, the gel is a poly-acrylamide gel. In some embodiments, the separation material has a pore size ranging from about 100 nanometers (nm) to about 200 nm. In some embodiments, the separation material slows down or prevents a portion of the plurality of nucleic acid molecules from permeating or diffusing through. In some embodiments, the second slot width is substantially equal to the first slot width. In some embodiments, the second slot width is greater than the first slot width. In some embodiments, the channel width measures between about 3.2 mm and 3.8 mm. In some embodiments, the first and second slot widths measure approximately twice as much as the channel width. In some embodiments, the first and second slots are substantially rectangular.

In some embodiments, a concentration region is disposed between the first slot and the second slot. In some embodiments, the first slot has a first slot height and the second slot has a second slot height. In some embodiments, the first slot height is greater than the second slot height. In some embodiments, the second slot height is substantially equal to the first slot height. In some embodiments, the nucleic acid molecules have a length ranging from about 45 kilobases (kb) to about 800 kb. In some embodiments, the bottom surface is a glass substrate. In some embodiments, the separation material does not comprise agarose, sodium alginate, gellan gum, or any combination thereof. In some embodiments, the device is not connected to a cooling apparatus. In some embodiments, the mesofluidic devices provided herein further include a third slot having a third slot width, wherein the third slot is configured to receive a separation material having a second porosity. In some embodiments, the mesofluidic devices provided herein further include a fourth slot having a fourth slot width, wherein the fourth slot is configured to receive a separation material having a third porosity. In some embodiments, the elongated channel is tapered.

In one aspect, provided herein are methods of eluting and concentrating a plurality of nucleic acid molecules, the method includes providing a mesofluidic device including: a device frame having a bottom surface upon which is defined a first reservoir comprising a first electrode, a second reservoir comprising a second electrode, the first and second electrodes configured for electrical connection, and an elongated channel extending between the first reservoir and the second reservoir, the elongated channel having a channel width; a first slot having a first slot width, the first slot configured to receive an insert, wherein the first slot intersects the elongated channel; and a second slot having a second slot width, the second slot configured to receive a separation material having a first porosity wherein the second slot intersects the elongated channel, wherein the first slot width and the second slot with width are greater than the channel width; depositing the insert comprising the plurality of nucleic acid molecules in the first slot; depositing the separation material in the second slot; adding a buffer solution to the elongated channel; applying an electrical voltage across the first and the second electrodes; eluting the plurality of nucleic acid molecules from the insert; and concentrating the plurality of nucleic acid molecules at a concentration region disposed between the first slot and the second slot.

In some embodiments, the plurality of nucleic acid molecules is deoxyribonucleic acid (DNA) molecules. In some embodiments, insert is an agarose gel. In some embodiments, the separation material is a poly-acrylamide gel. In some embodiments, placing the separation material comprises: inserting a first piece of polydimethylsiloxane (PDMS) at a first end of the second slot; inserting a second piece of PDMS at a second end of the second slot; adding acrylamide, bis-acrylamide, and an initiator between the first piece and the second piece of PDMS; and removing the first and second pieces of PDMS after polymerization of the separation material occurs.

In some embodiments, the methods further include adding a portion of the initiator to the bottom surface under the first and second pieces of PDMS. In some embodiments, the separation material has a concentration of acrylamide and bis-acrylamide that is twice as much as the concentration of an initiator. In some embodiments, the initiator is tetramethylethylenediamine (TEMED), ammonium persulfate (APS), or a combination thereof. In some embodiments, applying the electrical voltage comprises connecting an electrical wire to the first and second electrodes and a power supply. In some embodiments, the electrical voltage is between about 10 V and 30 V. In some embodiments, about 75% to 90% of the plurality of nucleic acid molecules is eluted from the insert. In some embodiments, the methods further include collecting the plurality of nucleic acid molecules at the concentration region. In some embodiments, about 35% to 75% of the plurality of nucleic acid molecules is collected at the concentration region. In some embodiments, the plurality of nucleic acid molecules is concentrated at an interface between the buffer solution and the separation material at the concentration region. In some embodiments, the method does not require cooling. In some embodiments, the separation material does not comprise agarose, sodium alginate, gellan gum, or any combination thereof. In some embodiments, the separation material has a pore size ranging from about 100 nanometers (nm) to about 200 nm. In some embodiments, the separation material slows down or prevents a portion of the plurality of nucleic acid molecules from permeating or diffusing through. In some embodiments, the nucleic acid molecules have a length ranging from about 45 kilobases (kb) to about 800 kb. In some embodiments, the bottom surface is a glass substrate.

All publications, patents, patent applications, and information available on the internet and mentioned in this specification are herein incorporated by reference to the same extent as if each individual publication, patent, patent application, or item of information was specifically and individually indicated to be incorporated by reference. To the extent publications, patents, patent applications, and items of information incorporated by reference contradict the disclosure contained in the specification, the specification is intended to supersede and/or take precedence over any such contradictory material.

Where values are described in terms of ranges, it should be understood that the description includes the disclosure of all possible sub-ranges within such ranges, as well as specific numerical values that fall within such ranges irrespective of whether a specific numerical value or specific sub-range is expressly stated.

Various embodiments of the features of this disclosure are described herein. However, it should be understood that such embodiments are provided merely by way of example, and numerous variations, changes, and substitutions can occur to those skilled in the art without departing from the scope of this disclosure. It should also be understood that various alternatives to the specific embodiments described herein are also within the scope of this disclosure.

BRIEF DESCRIPTION OF THE DRAWINGS

The following drawings illustrate certain embodiments of the features and advantages of this disclosure. These embodiments are not intended to limit the scope of the appended claims in any manner. Like reference symbols in the drawings indicate like elements.

FIG. 1C shows PLA devices were attached with double-sided tape to a glass slide and sealed with caulk around the edges to perform each experiment. FIGS. 1D and 1E show gel inserts with DNA were dyed with YOYO-1 and placed into the device. A given voltage (26.1 V) was applied to the device for a given period of time. Fluorescent images (FIGS. 1F and 1G) were taken throughout the experiment to capture the movement of the DNA.

FIG. 3A shows an image of a 3D printed device attached to a glass slide with double-sided tape and caulk. FIG. 3B shows a 3D printed device was produced to hold a polyacrylamide gel matrix in the roadblock section (RB) (also illustrated in FIG. 6B). Lambda DNA was embedded within a 0.5% agarose insert and placed into the device in the loading region (LR). The electrodes were placed in the wells (circles) and an electric field was applied (26.1-V) to concentrate DNA at the interface between the solution and gel. A montage of images was produced with ImageJ to illustrate the migration and concentration of lambda DNA on the 4× acrylamide roadblock in the 3D printed device. As illustrated, the acrylamide gel was able to concentrate most of the DNA at the acrylamide roadblock. FIG. 3C is a schematic illustrating an example mesofluidic device and electrodes with an arrow pointing in the direction of DNA migration. DNA insert was placed in the loading region (LR) and DNA was eluted into the channel (Ch) and then concentrated at the roadblock (RB). FIG. 3D is a graph showing the intensity of DNA in an insert versus time. FIG. 3E shows the intensity of the DNA concentrated at the interface between the solution and roadblock over time.

(FIG. 4A) Over the course of 5-experiments, the amount of DNA eluted from the insert was measured using two different methods. (Black) The fluorescent intensity of DNA was measured prior to the voltage (0-min.) and at 60-min. and background was subtracted to determine the ratio of DNA left in the insert after the completion of the experiment. The ratio was converted to the amount of DNA eluted based on the initial fluorescent intensity at 0 min. (Gray) After the experiment was completed; the insert was saved and compared to a standard calibration curve of DNA inserts with a dynamic range of DNA. (FIG. 4B) (Diagonal Strip) For those 5 experiments, the amount of DNA that was concentrated at the interface between a solution and acrylamide gel was measured with fluorescence intensity and converted to the amount of DNA concentrated. (Blue) The amount of DNA recovered was measured with a Nanophotometer.

Referring to FIG. 8A, the width was 3 mm and applied voltage was 40 V. For this device, some DNA molecules slowly migrated from the insert, but it was determined to be ineffective. Referring to FIG. 8B, the width was 5 mm, and the applied voltage was 60 V. For this device, the insert dislodged and migrated into the channel, therefore, it was determined to be ineffective. Referring to FIG. 8C, the width was 3.5 mm, and the applied voltage was 40 V. For this device, a majority of the DNA molecules migrated out of insert and into the channel. This device was determined to be the most effective.

Referring to FIG. 9A, the width of the channel was 3 mm and a voltage (20 V) is applied across the device to elute DNA. Over time, the intensity of the insert decreased slowly as the DNA molecules moved into the channel. A large amount of the DNA stayed in the insert. Referring to FIG. 9B, the width of the channel was 5 mm and 60 V was applied. Over time, the intensity of the insert decreased and then increased again when the insert started to move from the original position in the loading region. This may be due to electroosmotic flows in the device. The peak of DNA migration was at 4 minutes. Referring to FIG. 9C, the width of the channel is 3.5 mm and 40 V was applied. Over time, the insert decreased in intensity when the DNA molecules moved into the channel. The majority of the DNA molecules exited in the first 15 minutes.

(FIG. 10A) A funnel was used to try and concentrate DNA molecules at the narrowest point in the device. This did not concentrate DNA. (FIG. 10B) Two channels perpendicular to the main channel were created to decrease the effective electric field at the point between the channel and the concentration region (blue and green). The DNA filled up the concentration region between 5-10 minutes and then all DNA eluted from the region. (FIG. 10C) A triangle shape was utilized to trap DNA. Similar to (FIG. 10B) DNA filled up the concentration region and then by 20 minutes most DNA molecules left the region. (FIG. 10D) A bow tie was tested and similar to (FIG. 10B) and (FIG. 10D), DNA concentrated in the concentration region during 0-15 minutes, but then the DNA left. In all devices, the DNA did not remain in the concentration region.

DETAILED DESCRIPTION

Figure 14A:
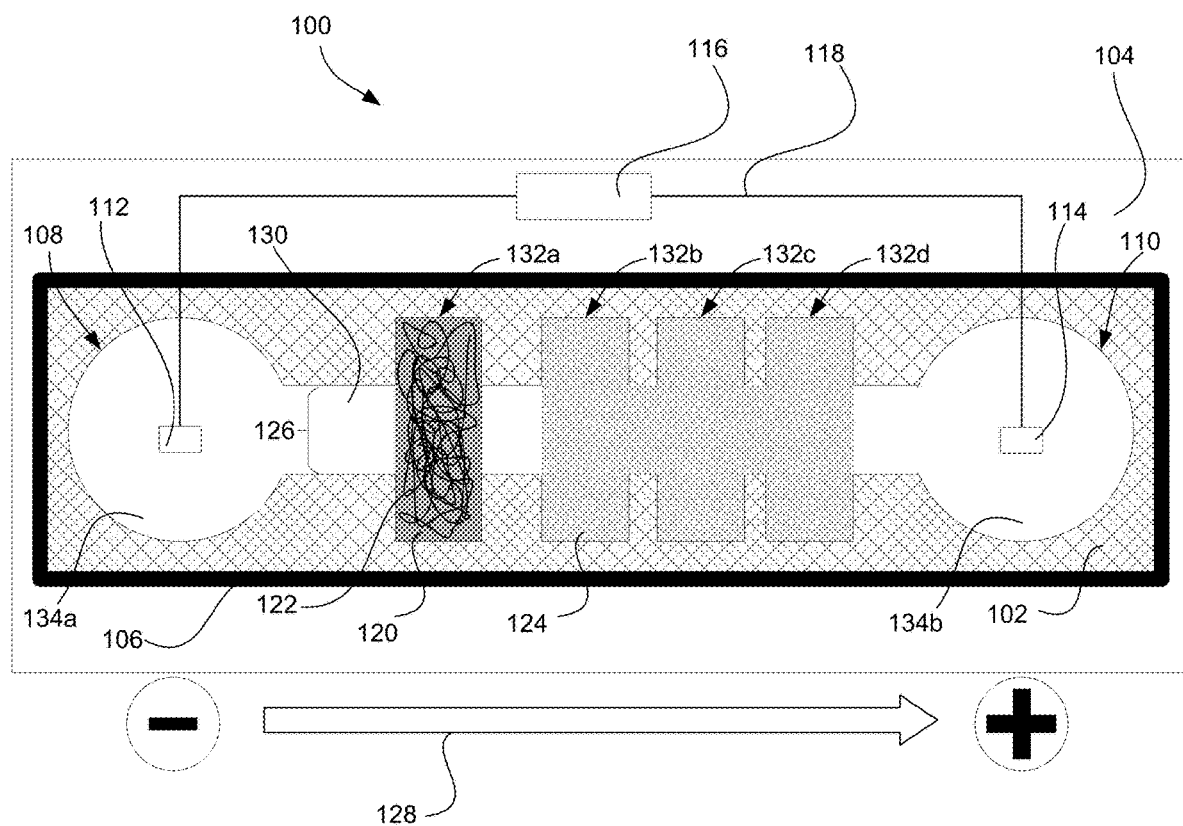
FIG. 14A is a schematic illustrating an example mesofluidic device showing a plurality of nucleic acids embedded within the insert.
Figure 14B:
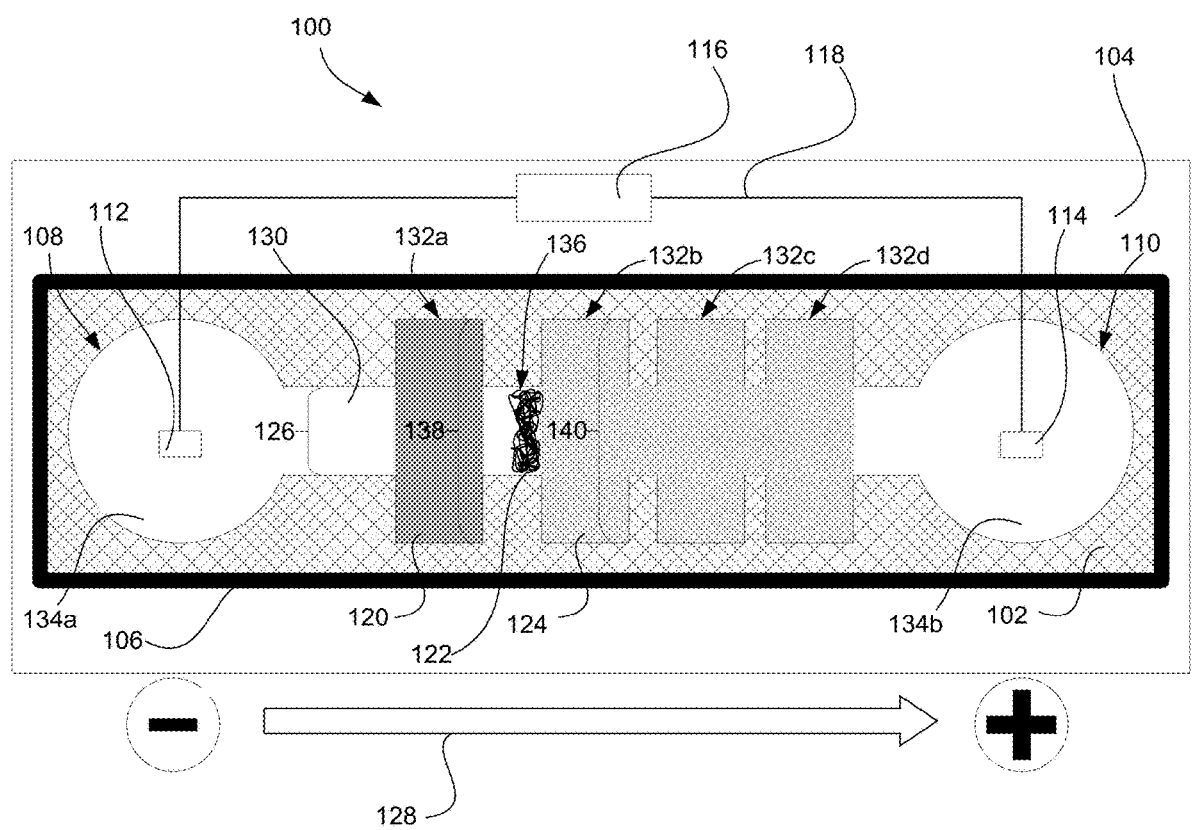
FIG. 14B is a schematic illustrating an example mesofluidic device showing a plurality of nucleic acids in the concentration region after having migrated out of the insert.

FIGS. 14A and 14B illustrate a top view of a three-dimensionally (3D) printed mesofluidic device 100 that can be used for eluting and concentrating a plurality of nucleic acid molecules. As used herein, the term "mesofluidic device" refers to a fluidic device that has a geometry in the millimeter (mm) to centimeter (cm) scale and can be used to contain and manipulate fluids at the milliliter (mL) scale.

Mesofluidic device 100 includes a device frame 102 having a bottom surface 104 upon which is defined a first reservoir 134a and a second reservoir 134b. In addition, the mesofluidic device 100 includes a first end 108, a second end 110, and an elongated channel 130 extending therebetween. The first end 108 includes the first reservoir 134a and the second end 110 includes the second reservoir 134b. The first reservoir 134a and the second reservoir 134b include a first electrode 112 and a second electrode 114, respectively, which are configured for electrical connections. The first reservoir 134a and the second reservoir 134b can have a diameter of about 8 mm, as shown in FIG. 6.

In some embodiments, bottom surface 104 is a glass slide. In some embodiments, bottom surface 104 is a planar substrate. In some embodiments, the bottom surface is a rectangular surface that measures about 1 inch by 3 inches. In some embodiments, the bottom surface is a rectangular surface that measures about 2 inch by 3 inches. A seal 106 can be applied along the perimeter of the PLA component 102 such that the seal 106 comes in contact with both the surface of the substrate 104 and the periphery of the PLA component 102, thereby preventing a fluid leakage. In some embodiments, seal 106 is caulk.

Furthermore, mesofluidic device 100 includes a first slot 132*a*, a second slot 132*b*, a third slot 132*c*, and a fourth slot 132*d* that intersect the elongated channel 130 at right angles (i.e., perpendicularly). The first slot 132*a*, the second slot 132*b*, the third slot 132*c*, and the fourth slot 132*d* have a first slot height, a second slot height, a third slot height, and a fourth slot height, respectively. As used herein, the slot height, refers to the measurement from the bottom surface 104 to the top surface 146 of the device frame 102, within the slot. In some embodiments, the first slot has a first slot height and the second slot has a second height. In some embodiments, the first slot height is greater than the second slot height. In some embodiments, the first slot height is greater than the second slot height. In some embodiments, the second slot height is substantially equal to the first slot height. In some embodiments, the mesofluidic device 100 has a first slot and a second slot having a surface area that is three times as large as the surface area of the first slot. In some embodiments, the mesofluidic device 100 has a first slot and a second slot having a surface area that is about three times as large as the surface area of the first slot. In some embodiments, the mesofluidic device 100 has a first slot and a second slot having a surface area that is about four or five times as large as the surface area of the first slot. In some embodiments, the mesofluidic device 100 has a first slot and a second slot having a length that is about three times as large as the length of the first slot. In some embodiments, the mesofluidic device 100 has a first slot and a second slot having a length that is about four or five times as large as the length of the first slot.

Figure 15:
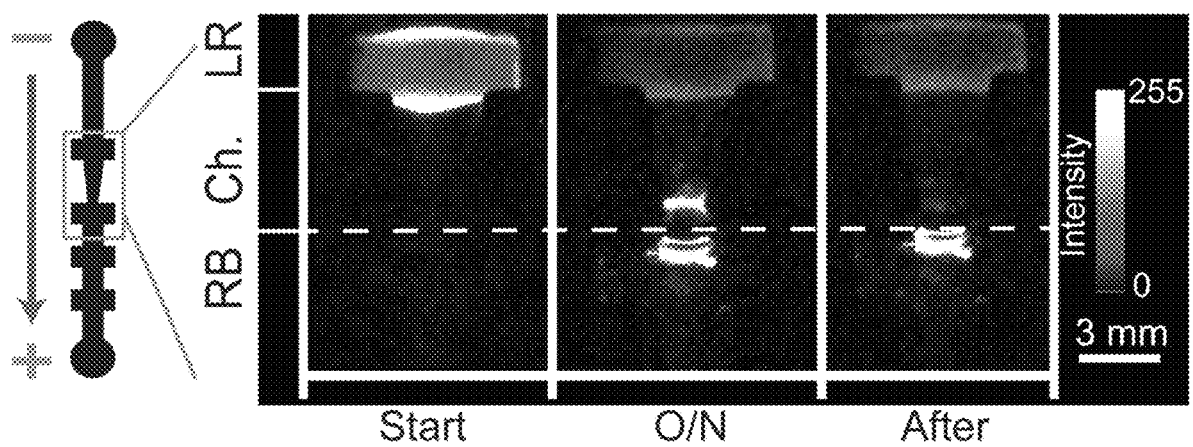
FIG. 15 illustrates a montage of a mesofluidic device having a tapered portion of the channel showing DNA eluting from a DNA insert and concentrating by the second slot including the separation material (e.g., the roadblock (RB)). The loading region (LR) and channel (Ch) as well as the detected fluorescence intensity of the labeled DNA is shown over a period of time.

The first slot 132*a* defines an insert region. The elongated channel 130 can have a channel width 126 of about 3.5 millimeters (mm). In some embodiments, the channel width 126 measures between about 3.2 mm and 3.8 mm. In some embodiments, the channel width 126 measures between about 1 mm and 10 mm. In some embodiments, the channel width 126 measures between about 1 centimeters (cm) and 10 cm. In some embodiments, the channel width 126 measures between about 10 cm and 100 cm. In some embodiments, a portion of the elongated channel 130 is tapered as shown in FIG. 15. The portion of the elongated channel 130 that can be tapered may be the portion positioned between the first slot 132*a* and the second slot 132*b*. In some embodiments, both ends of a portion of the elongated channel 130 can be tapered. As shown in FIG. 15, the elongated channel 130 has a tapered end that connects to the second slot 132*b* configured to receive the separation material 124.

The first slot 132*a* has a first slot width 138 that can be about 7 mm. In some embodiments, the first slot width 138 measures between about 1 mm and 10 mm. In some embodiments, the first slot width 138 measures between about 1 centimeters (cm) and 10 cm. In some embodiments, the first slot width 138 measures between about 10 cm and 100 cm.

The second slot 132*b*, the third slot 132*c*, and the fourth slot 132*d* have a second slot width 140, a third slot width 142, and a fourth slot width 144, respectively. The first slot width 138 and the second slot width 140 can be greater than the channel width 126. In some embodiments, the third slot width 142 and the fourth slot width 144 are greater than the channel width 126.

The second slot 132*b* has a second slot width 140 that can be about 7 mm. In some embodiments, the second slot width 140 measures between about 1 mm and 10 mm. In some embodiments, the second slot width 140 measures between about 1 centimeters (cm) and 10 cm. In some embodiments, the second slot width 140 measures between about 10 cm and 100 cm.

The third slot 132*c* has a third slot width 142 that can be about 7 mm. In some embodiments, the third slot width 142 measures between about 1 mm and 10 mm. In some embodiments, the third slot width 142 measures between about 1 centimeters (cm) and 10 cm. In some embodiments, the third slot width 142 measures between about 10 cm and 100 cm.

The fourth slot 132*a* has a fourth slot width 144 that can be about 7 mm. In some embodiments, the fourth slot width 144 measures between about 1 mm and 10 mm. In some embodiments, the fourth slot width 144 measures between about 1 centimeters (cm) and 10 cm. In some embodiments, the fourth slot width 144 measures between about 10 cm and 100 cm.

The measurements of the channel width 126, the first slot width 138, the second slot width 140, the third slot width 142, and the fourth slot width 144 mentioned above are representative measurements only as these measurements are dependent on the size, design, or both size and design of the mesofluidic device. In some embodiments, the second slot width 140 is substantially equal to the first slot width 138. In some embodiments, the second slot width 140 is greater than the first slot width 138. In some embodiments, the first slot width 138 second slot width 140 measure approximately twice as much as the channel width 126.

The first slot is configured to receive an insert 120. In some embodiments, the first slot 132*a* is substantially rectangular. Insert 120 can be substantially flushed with and disposed within the first slot 132*a*. Insert 120 can be a gel as described in the Supplemental Materials and Methods 1, Section 1.2. Insert 120 can further comprise a plurality of nucleic acid molecules and agarose. Non-limiting examples of materials that insert 120 can be made from include agarose, poly-acrylamide, alginate, and Gellan gum.

Similarly, the second slot 132*b*, the third slot 132*c*, and the fourth slot 132*d* are configured to receive a separation material 124. In some embodiments, the second slot 132*b*, the third slot 132*c*, and the fourth slot 132*d* are substantially rectangular. However, any suitable geometric or non-geometric shape can be used to receive the separation material. Non-limiting examples of shapes that can be part of the mesofluidic device 100 (e.g., to receive a separation material or an insert including a plurality of nucleic acid molecules) include a bow tie, a funnel, a circle, a triangle, a square, a hexagon, a pentagon, a tapered rectangle, and a curved channel. The second slot 132*b* is configured to receive a separation material 124 having a first porosity. In some embodiments, the separation material has a second porosity, and a third porosity. The mesofluidic device 100 can include separation materials with various porosities. For example, a plurality of nucleic acid molecules can be concentrated and collected using a separation material with a first porosity. Subsequently, the user can deposit the collected plurality of nucleic acid molecules onto the mesofluidic device with a separation material with a second porosity that is different than the first porosity, thereby concentrating a second plurality of nucleic acid material of a different size than the collected plurality of nucleic acid molecules. The user can repeat the process as necessary to concentrate and collect a plurality of nucleic acid material with a desired size range.

The first porosity can have a pore size ranging from about 100 nanometers (nm) to about 200 nm. In some embodiments, the first porosity can have a pore size ranging from about 5 to 100 nm. In some embodiments, the first porosity can have a pore size ranging from about 200 to about 500 nm. In some embodiments, the first porosity can have a pore size ranging from about 50 to about 600 nm. The second porosity can have a pore size ranging from about 100 nanometers (nm) to about 200 nm. In some embodiments, the second porosity can have a pore size ranging from about 5 to 100 nm. In some embodiments, the second porosity can have a pore size ranging from about 200 to about 500 nm. In some embodiments, the second porosity can have a pore size ranging from about 50 to about 600 nm. The third porosity can have a pore size ranging from about 100 nanometers (nm) to about 200 nm. In some embodiments, the third porosity can have a pore size ranging from about 5 to 100 nm. In some embodiments, the third porosity can have a pore size ranging from about 200 to about 500 nm. In some embodiments, the third porosity can have a pore size ranging from about 50 to about 600 nm.

The first separation material 124a, the second separation material 124b, and the third separation material 124c can be substantially flushed with and disposed within the second, third, and fourth slots 132b, 132c, and 132d, respectively. First, second, and third separation materials 124a-c can be a polyacrylamide gel as described in the Examples. In some embodiments, the mesofluidic device 100 has 1, 2, 3, 4, 5, 10, or more slots. In some embodiments, the mesofluidic device 100 has 1, 2, 3, 4, 5, 10, or more separation materials. The separation material can be a gel, a filter, or a physical barrier. In some embodiments, the gel is a poly-acrylamide gel. In some embodiments, the separation material does not include agarose, sodium alginate, gellan gum, or any combination thereof. In some embodiments, the separation material includes about 0.01% to about 10% of agarose, sodium alginate, gellan gum, or any combination thereof. In some embodiments, the separation material including more than about 0.01% to about 10% of agarose, sodium alginate, gellan gum, or any combination thereof does not slow down or prevent a portion of the plurality of nucleic acid molecules from permeating or diffusing through. In some embodiments, the filter is a membrane filter, a paper filter, or a metal filter. The separation material slows down or prevents a portion of the plurality of nucleic acid molecules from permeating or diffusing through. In some embodiments, the mesofluidic device 100 is not connected to a cooling apparatus.

FIGS. 14A and 14B further illustrate the migration of the plurality of nucleic acid molecules 122 through the elongated channel 130 into a concentration region 136. The concentration region 136 can be disposed between the first slot 132a and the second slot 132b. In some embodiments, the plurality of nucleic acid molecules 122 is a plurality of deoxyribonucleic acid (DNA) molecules. In some embodiments, the plurality of nucleic acid molecules 122 has a length ranging from about 45 kilobases (kb) to about 1 megabase (Mb). In some embodiments, the plurality of nucleic acid molecules 122 has a length ranging from about 45 kb to about 900 kb. In some embodiments, the plurality of nucleic acid molecules 122 has a length of about 48.5 kb. In some embodiments, the plurality of nucleic acid molecules 122 has a length ranging from about 45 kb to about 100 kb, from about 100 kb to about 200 kb, from about 200 kb to about 300 kb, from about 300 kb to about 400 kb, from about 400 kb to about 500 kb, from about 500 kb to about 600 kb, from about 600 kb to about 700 kb, from about 700 kb to about 800 kb, from about 800 kb to about 900 kb, or from about 900 kb to about 1 Mb. Mesofluidic device 100 can further comprise an electrical wire 118 electrically connecting the first electrode 112 and the second electrode 114 to a power supply.

In an aspect, the present disclosure provides a method of using a mesofluidic device for eluting and concentrating a plurality of nucleic acid molecules. The method includes providing a mesofluidic device (e.g., mesofluidic device 100). Next, the method includes placing the insert 120 including the plurality of nucleic acid molecules 122 in the first slot 132a. In some embodiments, the plurality of nucleic acid molecules 122 can be embedded within the insert 120. Next, the method includes placing the separation material 124a in the second slot 132b. In some embodiments, placing the separation material 124a in the second slot 132b includes: inserting a first piece of polydimethylsiloxane (PDMS) at a first end of the second slot 132b, inserting a second piece of PDMS at a second end of the second slot 132b, adding acrylamide, bis-acrylamide, and an initiator between the first piece and the second piece of PDMS, and removing the first and second pieces of PDMS after polymerization of the separation material 124a occurs. The method can further include adding a portion of the initiator to the bottom surface 104 under the first and second pieces of PDMS. The separation material has a concentration of acrylamide and bis-acrylamide that is twice as much as the concentration of an initiator. In some embodiments, the initiator is tetramethylethylenediamine (TEMED), ammonium persulfate (APS), or a combination thereof.

Next, the method includes adding a buffer solution to the elongated channel 130. In some embodiments, the volume of the buffer solution that is added to the elongated channel 130 ranges from about 1 milliliter (mL) to about 50 mL. Next, the method includes applying an electrical voltage across the first electrode 112 and the second electrode 114 using a power supply 116. In some embodiments, applying the electrical voltage includes connecting an electrical wire to the first and second electrodes and the power supply. Electrical wire 118 can be placed into the first reservoir 134a and into the second reservoir 134b and attached to the power supply 116. A total of 26.1 volts (V) can be applied to electrokinetically migrate the plurality of nucleic acid molecules 122 from the negative electrode 112 to the positive electrode 114, through the insert 120, and into the elongated channel 130 (see FIGS. 1D, 1E, 14A, and 14B). That is, the plurality of nucleic acid molecules 122 migrates in the direction of arrow 128 and accumulates at the concentration region 136. In some embodiments, the electrical voltage is between about 10 V and 30 V. In some embodiments, the electrical voltage is between about 10 V and 50 V. In some embodiments, the electrical field generated by the applied voltage has an electric filed strength of about 5 volts per centimeter (V/cm). In some embodiments, the electrical field generated by the applied voltage has an electric filed strength of about 2 V/cm. In some embodiments, the electrical field generated by the applied voltage has an electric filed strength ranging from about 1 V/cm to about 10 V/cm. It would be appreciated that any voltage could be used, provided that the separation material remains in a solid state (e.g., it does not transition from a solid to a liquid state). In some embodiments, the methods of the disclosure do not require cooling of the mesofluidic device, the insert, or the separation material. In some embodiments, the temperature of the separation material ranges from about 20° C. to about 37° C. throughout the elution and concentration process (i.e., while using the mesofluidic device). In some embodiments, the temperature of the insert including the plurality of nucleic acid molecules ranges from about 20° C. to about 37° C. throughout the elution and concentration process (i.e., while using the mesofluidic device). In some embodiments, the temperature of the separation material ranges from about 8° C. to about 20° C. throughout the elution and concentration process (i.e., while using the mesofluidic device) when using a buffer circulation system. In some embodiments, the mesofluidic devices include a buffer solution circulation system.

Next, the method includes eluting the plurality of nucleic acid molecules 122 from the insert 120 and concentrating the plurality of nucleic acid molecules 122 at a concentration region 136 disposed between the first slot 132a and the second slot 132b. The total elution and concentration time of the plurality of nucleic acid molecules by the mesofluidic device can be about 20 minutes (see, e.g., FIG. 3B). In some embodiments, the total elution and concentration time of the plurality of nucleic acid molecules by the mesofluidic device can be about 15 minutes. In some embodiments, the total elution and concentration time of the plurality of nucleic acid molecules by the mesofluidic device can range from about 10 minutes to about 60 minutes. In some embodiments, the elution time can take from about 1 day to about 2 days or longer. In some embodiments, about 75% to 90% of the plurality of nucleic acid molecules is eluted from the insert. The methods can further include collecting the plurality of nucleic acid molecules 122 at the concentration region 136. In some embodiments, about 35% to 75% of the plurality of nucleic acid molecules 122 is collected at the concentration region 136. In some embodiments, a first portion of the plurality of nucleic acid molecules 122 is collected at the concentration region 136 and a second portion is collected from the separation material 124. In some embodiments, the plurality of nucleic acid molecules 122 is concentrated at an interface between the buffer solution and the separation material 124 at the concentration region 136. The plurality of nucleic acid molecules 122 can be concentrated in a total volume of about 75 to about 750 microliters (µL), once the fluid within the first reservoir 134a and the second reservoir 134b is drained prior to collection.

EXAMPLES

Example 1—Fabrication of 3D Printed Mesofluidic Devices 3D printed mesofluidic devices 100 were designed in AutoCAD and exported to Cura (Ultimaker software) to determine the print speed, fill-in, adhesion, etc. (FIGS. 1, 14A, and 14B). Devices were then printed on an Ultimaker2 or Ultimaker3 3D printer (FIGS. 1A-1C) using polylactic acid (PLA) material. Device dimensions are located in FIG. 6. After the print was completed, double-sided tape was placed on the bottom of the device, minus the channel area, and adhered to 2×3 in. glass slide. Caulk was applied to the peripheral edge of the device to seal the device to the glass slide.

Example 2—Polymerization of Polyacrylamide Gels in PLA Channels

A matrix was set up of different amounts of acrylamide/bis solution, TEMED, and APS to determine how quickly the polyacrylamide gel would polymerize in our PLA devices. (Information about materials is located in the Supplemental Materials and Methods 1, Section 1.1.) A 1× acrylamide/bis and 1×TEMED/APS solution contained 111 µL 30% 29:1 or 19:1 acrylamide/bis solution, 889-µL $H_2O$, 7.5-µL 10% APS, and 0.8-µL TEMED. For each different concentration, the acrylamide/bis solution or TEMED/APS solution was increased. 1× was used as a starting point for the matrix, since it was utilized in Dimalanta et al. [9]. PLA channels were 3D printed using an Ultimaker2 or Ultimaker3 printer. The channels either had a PLA bottom or were open (FIG. 7).

Figure 2:
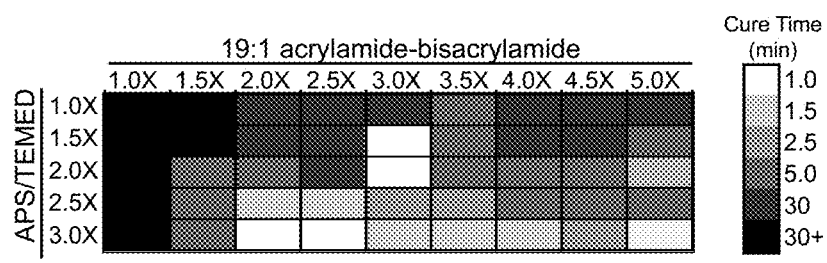
FIG. 2 shows the determination of polymerization time of acrylamide-bis gel in PLA devices. A 3D printed polylactic acid (PLA) channel was printed and attached to a glass slide. (mesofluidic device used shown in FIG. 7B). 30% 19:1 Acrylamide-Bis was mixed with water, TEMED, and APS in an Eppendorf tube. 1×19:1 acrylamide-bis solution and 1×TEMED/APS was added to the PLA device and the time it took for the solution to polymerize was measured by poking/lifting the gel to determine if the gel had polymerized. Depending on the curing time, a color was assigned for each time.

The channels that were open were affixed to the glass slide using double-sided tape and caulk. Once the channels were completed, the acrylamide solution was prepared by adding acrylamide/bis and water to an Eppendorf tube and the solution was degassed for 15-min. Next, APS and TEMED were added to the solution, respectively, and the solution was vortexed for 15-sec. The solution was then pipetted into PLA channels and the gel was checked with a glass hook by poking and then lifting the gel up to determine if the polyacrylamide gel had polymerized (FIG. 2).

Example 3—Preparation of Polyacrylamide Gel Roadblock

A 4× acrylamide-bis solution and 2×TEMED/APS was utilized to make the roadblocks due to the curing time and pore size. To make a dam to hold the acrylamide gel, PDMS pieces were wedged into the channel to keep the acrylamide in a specific region. In order to make these pieces, PDMS was mixed with a 10:1 pre-polymer to catalysis ratio, poured into an empty petri dish and cured at 60° C. overnight. The pieces were cut from the petri dish to be slightly larger than the channel width. 1-2 µl of TEMED was placed on the bottom of the device and the PDMS pieces were wedged into the device to create a dam, so the acrylamide solution would not leak out. A 4× acrylamide-bis solution and 2×TEMED/APS solution was made and loaded into the concentration region to cure. The device was placed in a humidified box at 4° C. overnight. The following day, excess polyacrylamide gel was removed from the device with a needle adaptor so only the specified area for the roadblock remained. Alternatively, earlier versions of the roadblock had the acrylamide solution poured into the whole device and then the gel was cut out with a needle. Both methods were used in this work.

Example 4—Elution and Concentration of DNA, Imaging and Analysis

A fluorescently stained DNA insert was placed in the loading region within the 3D printed device (Supplemental Materials and Methods 1, Section 1.2). If the device had an acrylamide roadblock, that step would have been completed the previous day. The channel was then loaded with 1×TE buffer, placed on top of a blue light transilluminator, platinum electrodes were added to each well, and an orange filter was placed in between the device and the vertically mounted Canon EOS Rebel T3I camera. Once the device was set up, a voltage was applied (26.1 V) using a across the device to move DNA molecules from the insert to the roadblock. Images were taken at discrete time points. Finally, images were analyzed with ImageJ to determine the amount of DNA leaving an insert and concentrating at the roadblock [20].

Example 5—Developing 3D Printed Mesofluidic Devices

In order to develop a mesofluidic device to elute and concentrate DNA, rapid prototyping and a device with a transparent bottom were required. Through many iterations, the most consistent method to create a device with a transparent, non-fluorescent bottom and fast prototyping was attaching a 3D printed device to a glass slide with double-sided tape, minus the channel region (FIG. 1). The device was designed in AutoCAD and then loaded on Cura to convert it into a format for our 3D printers and printed.

Figure 1A:
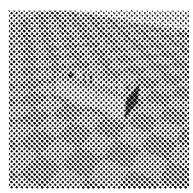
FIGS. 1A, 1B, 1C, 1D, 1E, 1F and 1G illustrate an example device design and loading scheme. The production of each device started with a design in AutoCAD. Files were then converted, using Cura software (FIG. 1A), and printed with an Ultimaker2 or Ultimaker3 printer (FIG. 1B).
Figure 1B:
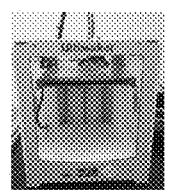
Figure 1C:
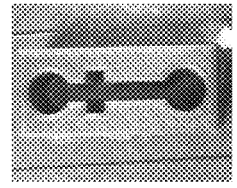
Figure 1D:
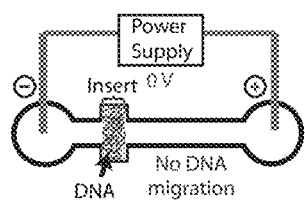
Figure 1E:
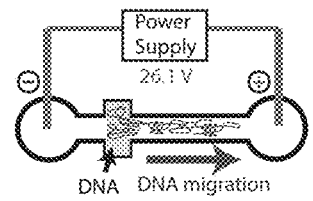
Figure 1F:
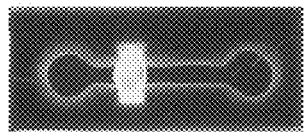
Figure 1G:
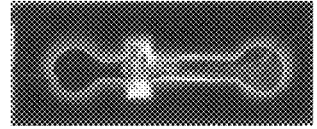
Figure 8A:
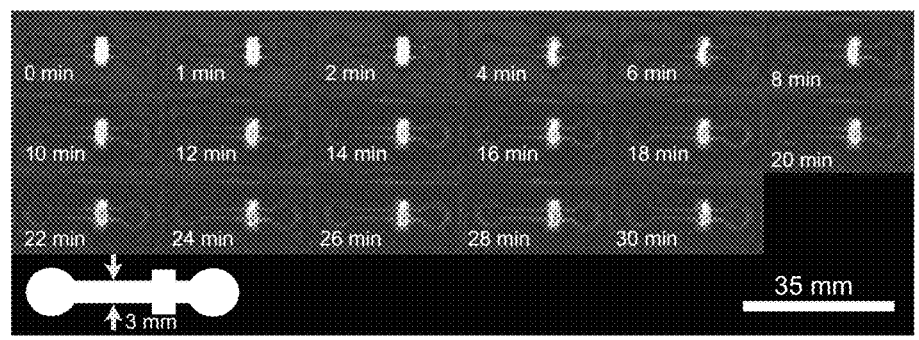
FIGS. 8A, 8B, and 8C show time lapse imaging of a 3D printed device to determine the width of the channel. Collections of fluorescent images (montage) were collected over a period of time (0-30 min.). The device was placed on a blue light transilluminator to excite the YOYO-1 dye and the emission of the dye was collected with a Canon camera. In order to determine the width of the device that was used for future prototypes, a series of images were compiled to show what occurred during the 30 minutes to determine which device eluted the most DNA, and determined if the insert stayed in place. All images were processed with ImageJ.
Figure 8B:
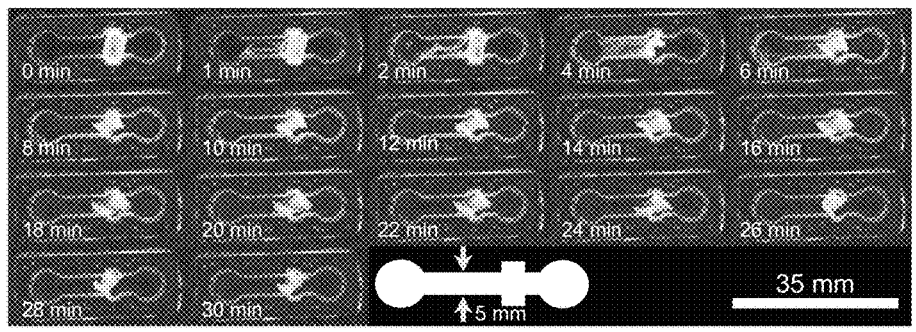
Figure 8C:
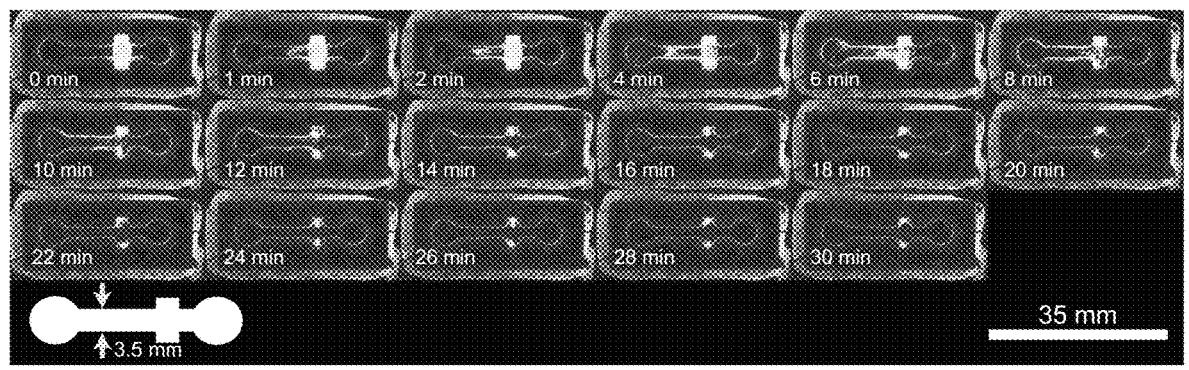
Figure 9A:
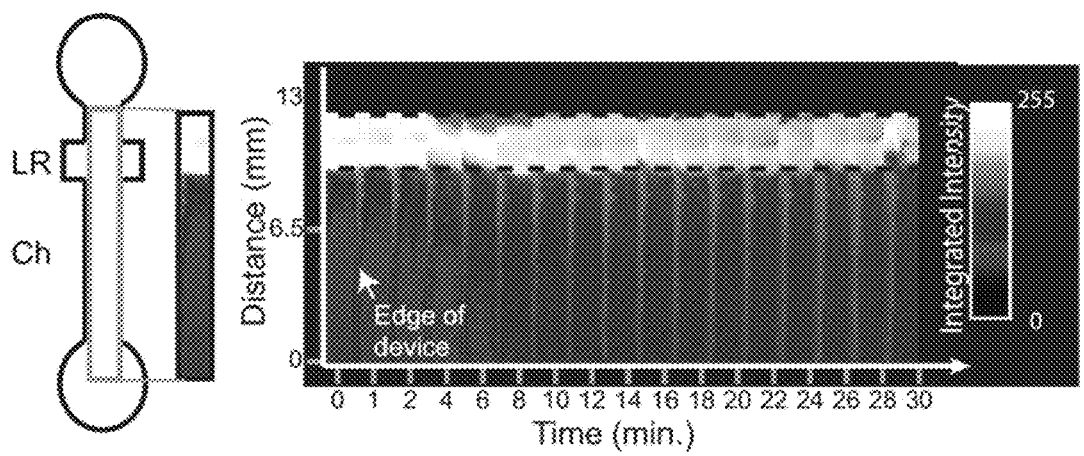
FIGS. 9A, 9B and 9C illustrate a montage of the 3D printed channel to show DNA eluting from a DNA insert. Each device has a montage for each image and is stacked next to each other, so the loading region (LR) and channel (Ch) could be observed in one 2D picture over a period of time. Using the pictures from FIG. 6, a montage was created to show DNA in the insert and channel.
Figure 9B:
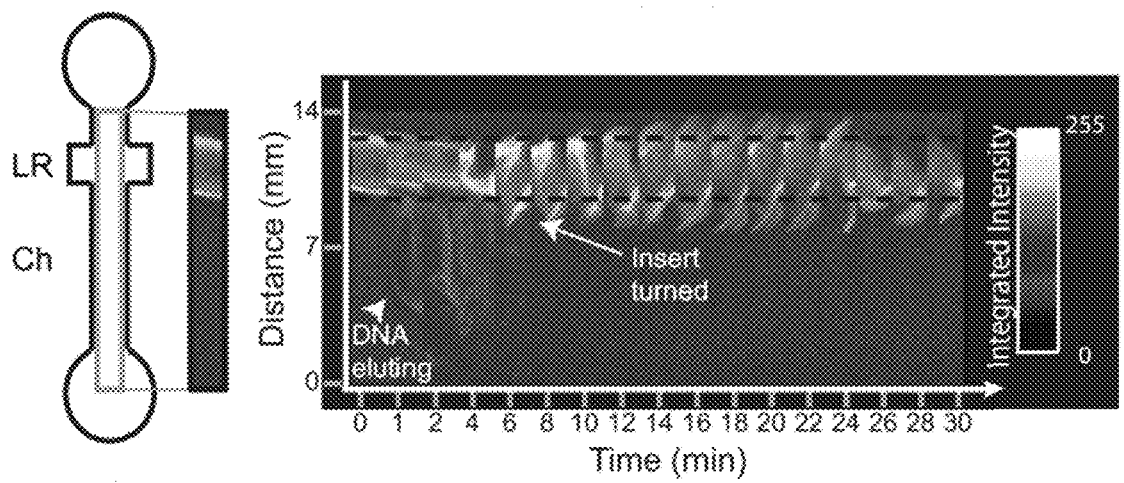
Figure 9C:
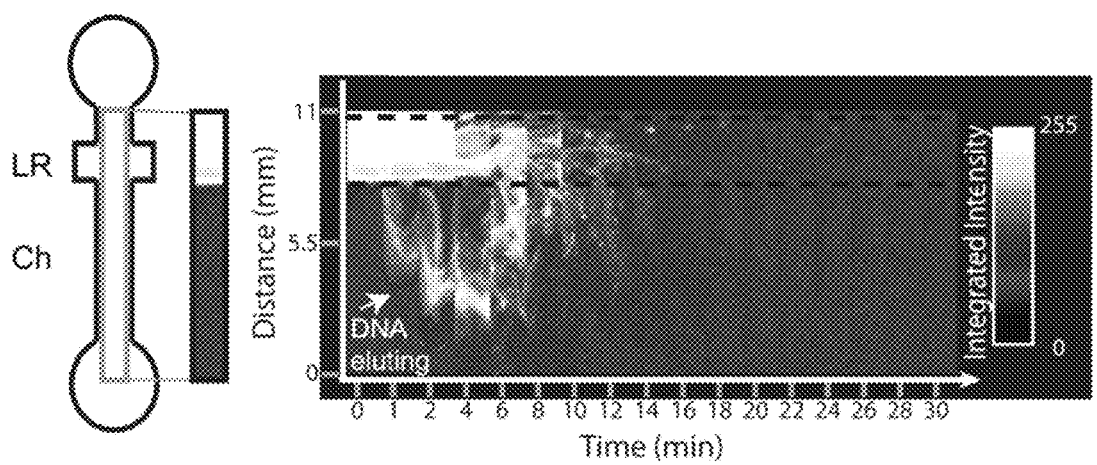
Figure 10A:
FIGS. 10A, 10B, 10C, and 10D are schematics illustrating example mesofluidic devices having insert regions (shaded regions) and concentration regions.
Figure 10B:
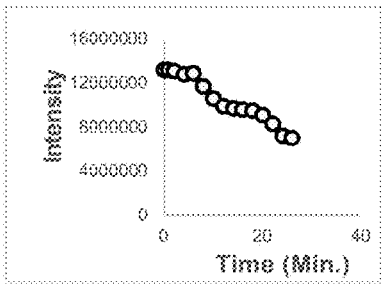
Figure 10C:
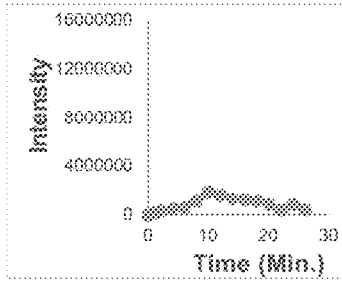
Figure 10D:
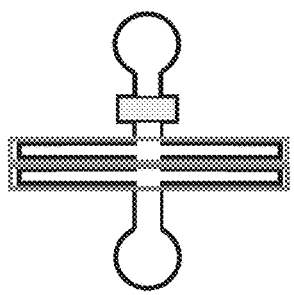
Figure 10E:
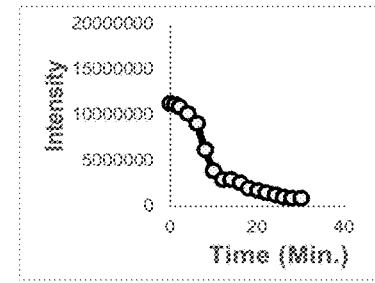
FIGS. 10E, 10F, 10G, and 10H are graphs showing the fluorescence intensities of labeled DNA at corresponding DNA insert regions.
Figure 10F:
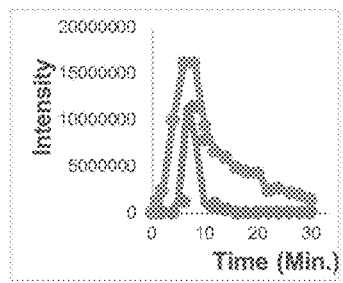
Figure 10G:
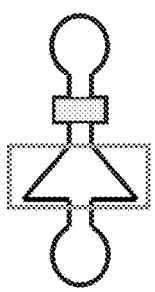
Figure 10H:
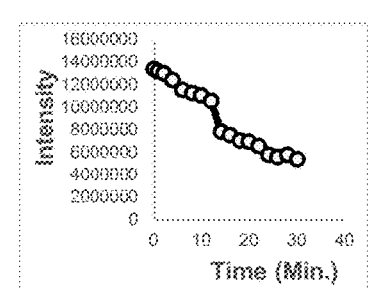
Figure 10I:
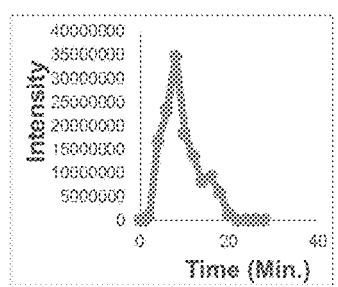
FIGS. 10I, 10J, 10K, and 10L are graphs showing the fluorescence intensities of labeled DNA at corresponding DNA concentration regions. Different types of devices were utilized to concentrate DNA. The yellow region highlights the insert and the intensity was recorded over time. Applying 26.1 V, the fluorescence intensity was measured for eluted (yellow box) and concentrated DNA (blue and green boxes) and shown in the figures to the right of each device.
Figure 10J:
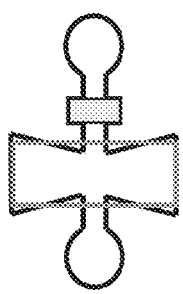
Figure 10K:
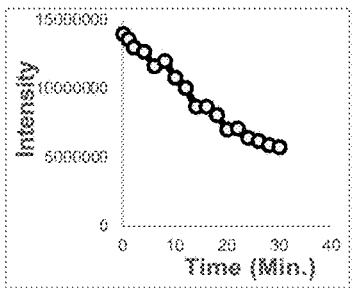
Figure 10L:
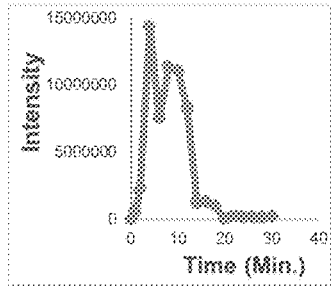
Figure 11A:
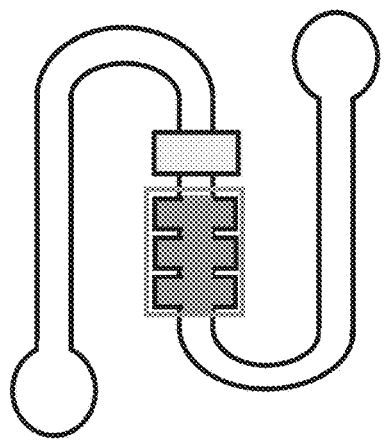
FIGS. 11A and 11B are schematics illustrating example mesofluidic devices having insert regions and concentration regions.
Figure 11B:
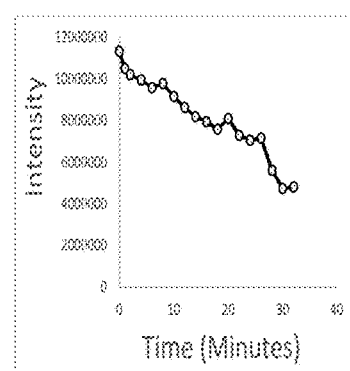
Figure 11C:
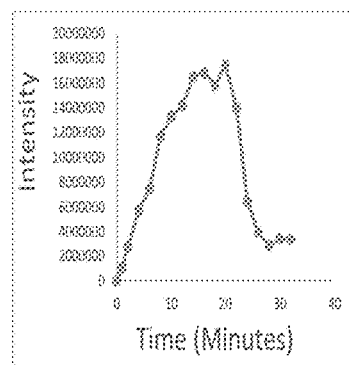
FIGS. 11C and 11D are graphs showing the fluorescence intensities of labeled DNA at corresponding DNA insert regions.
Figure 11D:
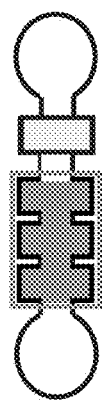
Figure 11E:
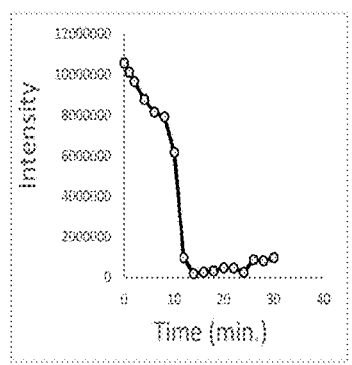
FIGS. 11E and 11F are graphs showing the fluorescence intensities of labeled DNA at corresponding DNA concentration regions. Different types of matrices were utilized to create a region to concentrate DNA molecules. DNA was eluted using 26.1 V for a specific time period. The fluorescence intensity was measured and plotted to the right of each device for the DNA insert region (yellow) and the concentration region (blue box). Gray indicates where the gel was located. (A) Three 0.25% sodium alginate (to impart a negative charge in the insert) and 0.5% HGT agarose inserts were placed in the concentration region (gray) to try and concentrate DNA. These inserts were unable to stop the progression of DNA, so the DNA moved through the inserts. (B) Three 0.75% Kelcogel LT100 and 0.25% HGT agarose inserts were tested and the concentration region was unable to trap DNA to concentrate it.
Figure 11F:
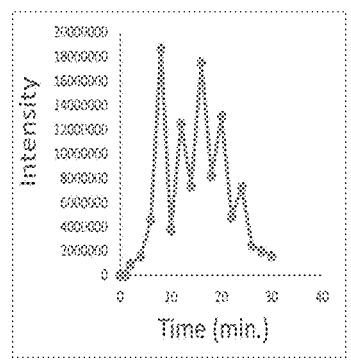

First, the channel width of the device was varied to determine the optimal channel width, so the insert stayed in the original location and eluted the most DNA. The 3D device was assembled with a glass bottom and lambda DNA insert stained with YOYO-1 was placed into the loading region of a device and the device was filled with 1×TE. Platinum wires were placed into the reservoirs and attached to a power supply. 26.1 volts (V) was applied to electrokinetically migrate DNA through the insert into the channel (FIG. 1D, 1E). A variety of different voltages were applied and 26.1 V was the most ideal voltage for out experiments due to the amount of time needed to run an experiment, but did not require a cooling apparatus. A montage (images collected over 30-min. and placed sequentially in the same image) is seen in FIGS. 8 and 9. In FIG. 9, the channel image is cropped and placed next to each image to show elution of DNA over the course of the experiment and to see, in greater detail, DNA eluted from the insert. Channel width was varied from 3.0 to 5.0 mm. For a width of 3.0 mm, DNA elution was minimal and a width of 5.0 mm caused the insert to slip during the course of the experiment, so it rotated and moved into the channel. The movement of the insert may be due to electroosmotic forces. A width of 3.5 mm allowed DNA to migrate into the channel, while the insert stayed in the original location, and was chosen for all future devices.

Example 6—3D Printed Devices to Concentrate DNA

A variety of different devices were designed to concentrate DNA by a 3D printed concentration region or a matrix that decreased the movement of DNA. An insert with stained DNA was loaded into a device, as well as the gel matrix if it was used to concentrate DNA (Kelcogel, agarose, sodium alginate). Next, 1×TE was added, so the device was full and platinum electrodes were placed in the reservoirs. 26.1V was applied and images were taken over a period of time to determine the amount of DNA that was eluted from the insert and the amount of DNA that was concentrated. In FIG. 6, the device dimensions for all devices are listed. In FIG. 10 (graph, yellow circles), for each device, DNA eluted. In FIG. 10, a funnel, perpendicular channel, triangle and bow tie were created to trap DNA. However, minimal amount of DNA was concentrated. The perpendicular channel (highlighted by the blue and green box) and triangle were able to trap DNA in the concentration region for several minutes, but eventually DNA migrated from the concentration region towards the electrode. Therefore, a concentration region required a physical barrier to inhibit or slow down the progression of DNA.

Next, a physical barrier was implemented to determine if a matrix could stop or slow down the progression of DNA in a channel. The following matrices were tried: 2% agarose, 0.5% agarose/0.25% sodium alginate, and 0.75% Kelcogel LT100/0.25% agarose. To impart a negative charge on the gel matrix, sodium alginate and Kelcogel LT100 were tried to induce an electroosmotic flow to concentrate DNA at a given area. The 2% agarose allowed DNA to move through the matrix without stopping (not pictured). Alginate and Kelcogel allowed DNA to concentrate for ~20-min. before DNA migrated through the matrix (FIG. 11). Using these matrices, DNA concentrated for a brief period of time, but DNA eventually migrated through the matrix.

Example 7—Polymerization of Polyacrylamide in 3D Printed Devices

The pore size of agarose was too large to inhibit the migration of DNA [21], so it was theorized that smaller pore sizes of polyacrylamide would stop the progression of DNA to create a roadblock. Dimalanta et al. used a polyacrylamide gel that was used as the basis for the original 1× solution [9]. However, it was found that the original 1× concentration of polyacrylamide and 1×TEMED/APS would not fully cure within a PLA device, so a matrix of different concentrations of acrylamide-bis solutions (29:1 or 19:1; acrylamide:bisacrylamide), TEMED and APS were varied to determine a set of solutions that would polymerize in our PLA devices. In order to determine how quickly the gel polymerized, each solution was added to a 3D printed channel (FIGS. 7A and B) with either the bottom made out of PLA or glass. To test if the gel polymerized, the gel was poked with a sealed-end glass pipette at each time point (FIG. 2 and FIG. 7). As the APS/TEMED mixture increased, the polymerization time decreased. As the acrylamide bis-acrylamide mixture increased, the polymerization time decreased, but not to the same extent that changing the APS/TEMED mixture did. Formation of the polymer was initiated by APS, which formed free radicals and TEMED acted to stabilize free radicals and promoted polymerization. 4× acrylamide-bis solution and 2×APS/TEMED were chosen, as the polymerization times allowed us to add the solution to the device without it curing too quickly.

Additionally, the qualitative effect of PLA was also tested to determine what role PLA had on the polymerization of acrylamide in channels with a PLA bottom versus glass bottom. PLA must slightly inhibit the formation of polyacrylamide at the surface of the plastic due to the longer polymerization times. Additionally, the original 1× acrylamide-bis and 1×APS/TEMED did not fully polymerize after 24 hrs. Further research would be needed to determine why PLA slightly inhibited the formation of polyacrylamide.

Example 8—Creating an Acrylamide Gel Roadblock

Figure 3A:
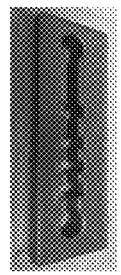
FIGS. 3A, 3B, 3C, 3D, and 3E show time-lapse imaging of DNA eluted and concentrated with an acrylamide roadblock and the mesofluidic device used for the same experiment.

Utilizing a 4× acrylamide-bis and 2×APS/TEMED solution, a roadblock was created inside a 3D printed mesofluidic device by using PDMS dams that fit on either side of the concentration region to hold the acrylamide gel in that location, while it cured (FIG. 3A). In order to prevent the acrylamide mixture from leaking out under the bottom of the PDMS, 1-2-μl of TEMED was added to the bottom, so the gel would polymerize quickly if it started to leak. Earlier versions of the acrylamide roadblock had the whole device full of the cured polyacrylamide gel and then sections were removed with a needle.

Figure 3B:
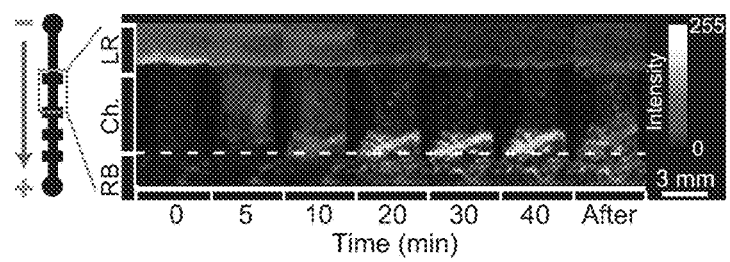
Figure 3C:
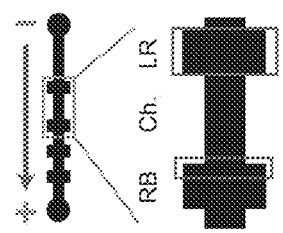
Figure 3D:
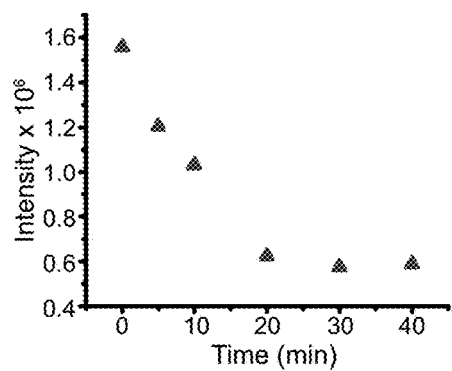

Acrylamide solution was mixed and added between the PDMS pieces then cured overnight in a humidifier box at 4° C. A YOYO-1 stained DNA insert was loaded into the loading region (LR) and the rest of the channel was loaded with 1×TE buffer. Platinum wires were added to the reservoirs and connected to the power supply. A montage of time lapsed images of the loading region (LR), channel, (Ch), and roadblock (RB) are shown in FIG. 3B, and the fluorescence intensity was measured of the insert region (blue box of FIG. 3C) to determine how much DNA left, as shown in FIG. 3D.

Figure 3E:
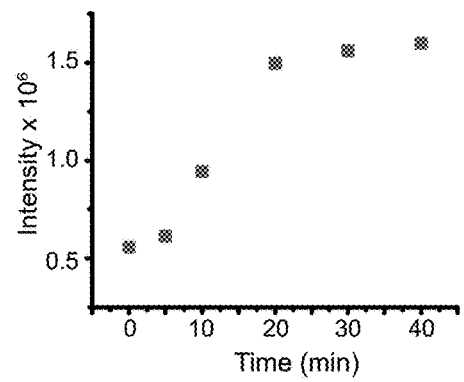

The concentration region's fluorescence intensity was also measured to determine how much DNA concentrated in the concentration region (red box of FIG. 3C), as shown in FIG. 3E.

At 0-min., DNA was in the loading region, but after 20-min., most of the DNA was concentrated at the roadblock region (dotted line). The pore size of the acrylamide is ~100-200-nm in size based on the % T and % C using data from Stellwagen et al.[21] DNA may have concentrated at the interface between the gel and the solution due to a decrease of DNA mobility between the gel and the solution. Also, DNA threading into the pore will take some time, further slowing down the progression of DNA. Some DNA embeds in the acrylamide gel, where other DNA might be partially in the gel with part of the DNA in solution. To allow for DNA that is partially inserted into the gel to unravel, the voltage is turned off for 20-min. to allow for DNA relaxation into solution before removing the solution. It was found that with agarose inserts, DNA migrated fairly quickly through the agarose gel matrix, but with acrylamide, DNA that entered the gel only migrated into the first few mm of the gel and stopped either through tangling around obstacles within the matrix or due to the amount of time the experiment was run for. The fluorescence intensity was plotted against time to show that as time increased, the fluorescence intensity of the loading region decreased due to DNA leaving the agarose insert and as time increased for the roadblock region, the fluorescence intensity increased as DNA concentrated at the roadblock region.

Figure 12:
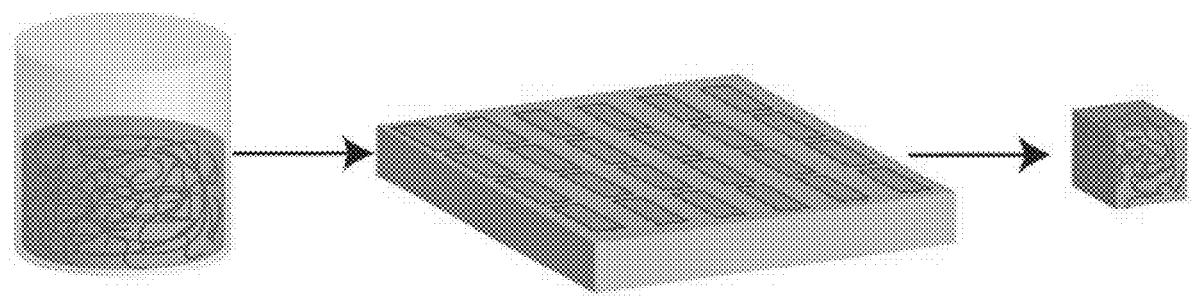
FIG. 12 is a schematic illustrating the process for making DNA inserts. A 0.5% solution of HGT agarose is boiled, cooled and mixed with DNA. The agarose-DNA solution was added to a 3D printed insert mold and the solution was cooled to solidify the agarose. Once the inserts were solidified, they were removed from the mold and placed into an Eppendorf tube and 200 µl 1×TE is added.
Figure 13:
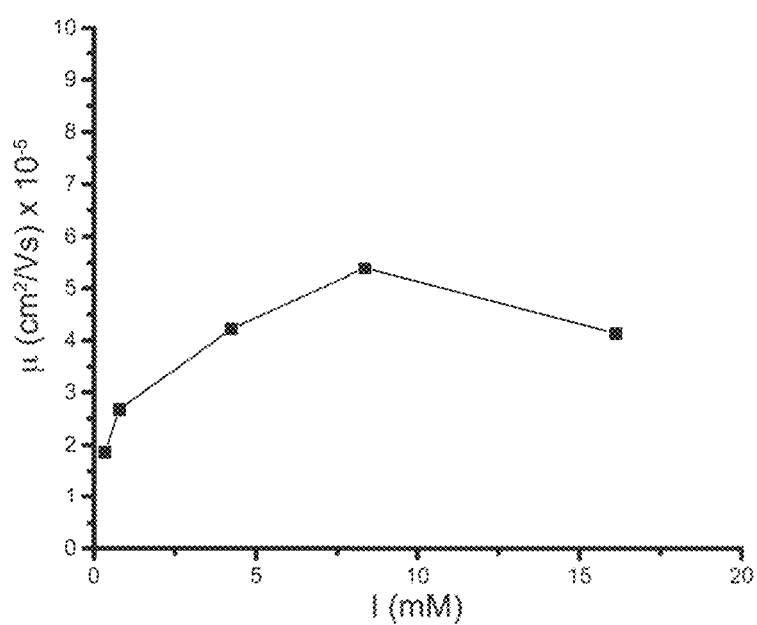
FIG. 13 is a graph showing the overall mobility of bromophenol blue determined in a dynamic range of ionic strength solutions. In order to determine the free solution mobility of DNA in a variety of solutions in acrylamide gel, 29:1 acrylamide gel in various percentages was created and plotted using a Ferguson plot and the y-intercept was obtained and used for the free solution mobility ($\mu$) at a given ionic strength (I). The free solution mobility is shown above for each ionic strength. The mobility decreased as the ionic strength decreased from ~9 mM, which is similar to what was found in Lallman et al. in agarose gel.

In a separate set of experiments, 5 devices were run for 1 hr. to determine the elution, concentration, and recovery rate. To determine the amount of DNA eluted from an insert and concentrated at a roadblock, each insert had 2-μl of 585-ng/μl lambda DNA added (FIG. 12) and was stained with YOYO-1 for a 1:4 (dye to DNA bp) ratio, overnight. The DNA insert was placed into a device with a roadblock and immersed in 1×TE buffer and imaged every 15-min. The 1×TE was chosen, as it had one of the highest free solution mobilities of DNA (Supplemental Materials and Methods 1, Section 1.4, FIG. 13), similar to what was found in Lallman et al. [22]. Once the electric field was turned off, DNA in the solution stayed and DNA that had one end in the gel and the other end in solution slowly relaxed into the solution due to entropy. The mobility difference and the size of the acrylamide pores slowed down DNA from entering into the gel. This difference allowed DNA to concentrate between the acrylamide and solution.

Figure 4A:
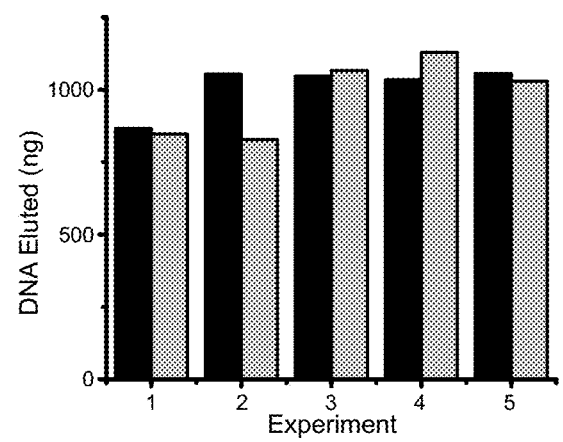
FIGS. 4A and 4B are graphs showing the amount of DNA that was eluted and concentrated.
Figure 4B:
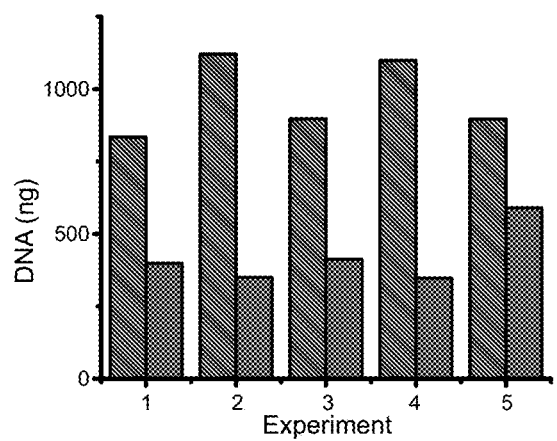

The fluorescence intensity of DNA was compared at 0 and 60 min. to determine the amount of DNA eluted from the insert (86%±7% or 1010±80 ng) (FIG. 4A). Given the data in FIG. 4, the elution of DNA was reproducible with a relative standard deviation (RSD) of 8%. Additionally, the amount of DNA remaining in an insert after the completion of the experiment was determined by comparing the insert intensity to known amounts of DNA within an insert (84%±11% or 1000±100 ng). The amount of DNA concentrated at the roadblock was measured by fluorescence intensity (83%±11% or 970±130 ng) (FIG. 4B) and compared to the original intensity at 0-min. to determine the amount at the roadblock. The amount recovered was measured with a Nanophotometer, and compared to the amount of eluted DNA also determined by fluorescence intensity, was 45±14% (RSD=31%). The rest of the DNA was embedded in the acrylamide. Our recovery was better than Amicon filters in Garvin et al.; average recovery rate of Amicon filters at 800 g for 6 samples was 38±11% (RSD=28%) [17]. The relative standard deviation of our device is similar to the Amicon filter data published by Garvin et al [17] and our data was reproducible. However, there are several factors that can be optimized to improve the recovery of DNA for our concentration device such as concentration time and modifying the acrylamide gel. Once DNA is concentrated in our device, it could be displayed in nanoslit or on a surface for Nanocoding.

Figure 5:
FIG. 5 shows a restriction digest of DNA concentrated at the acrylamide roadblock. A restriction digest experiment with HindIII was performed to determine if the recovered lambda DNA was full length. Lane-1 contained the recovered fluorescently stained DNA from our 3D printed device and Lane-2 contained stock lambda DNA stained with YOYO-1 (Control) and both were digested with HindIII.
Figure 6A:
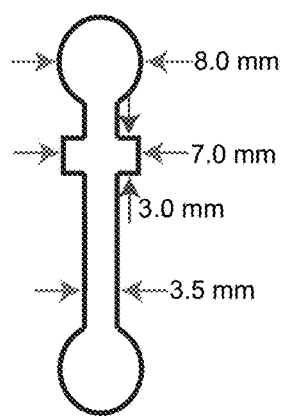
FIGS. 6A, 6B, 6C, 6D, 6E, 6F, and 6G are schematics illustrating example mesofluidic devices tested to elute and concentrate DNA molecules. The measurements of the original design (FIG. 10A) are shown to give dimensions of the insert and channel width of the device. In (FIG. 10B-10G), the dimensions of the concentration region are shown. The gray region is where the gel resides.
Figure 6B:
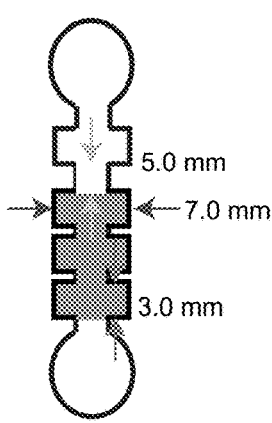
Figure 6C:
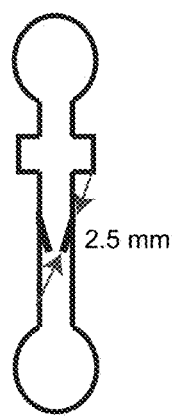
Figure 6D:
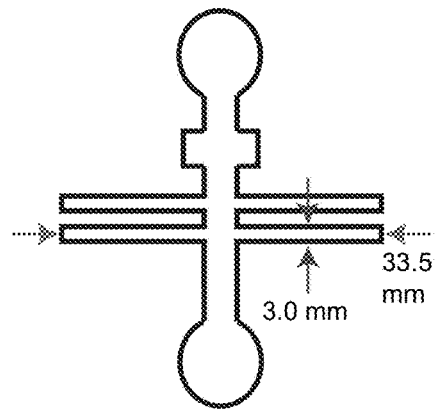
Figure 6E:
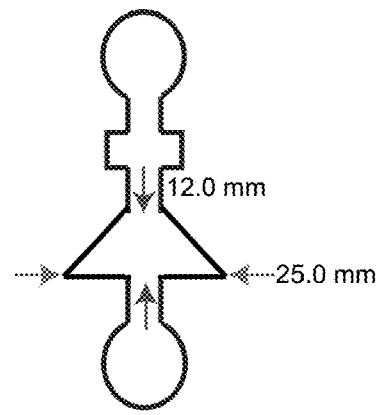
Figure 6F:
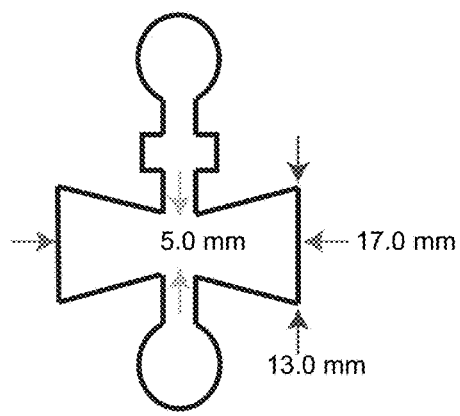
Figure 6G:
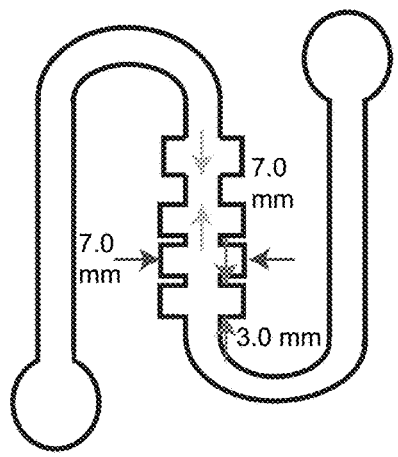
Figure 7A:
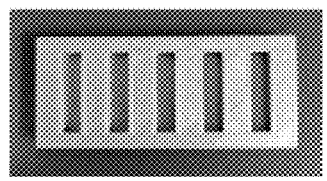
FIGS. 7A and 7B show a 3D printed PLA channel was printed and either had a printed PLA bottom (FIG. 7A) or it was attached to a glass slide with double sided tape and caulk (FIG. 7B).
Figure 7B:
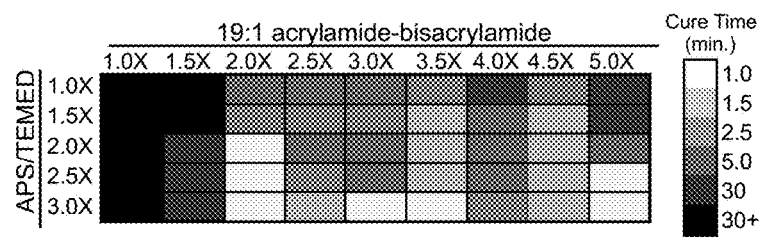
Figure 7C:
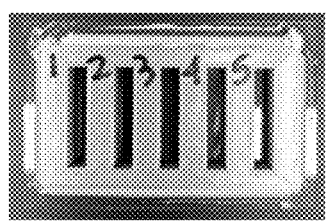
FIGS. 7C, 7D, and 7E show the determination of polymerization time of acrylamide-bis gel in PLA devices with a printed PLA bottom or attached to a glass slide. 30% 19:1 or 29:1 acrylamide-bis solution was mixed with water, APS, and TEMED in a tube and added to the PLA device. For a 1× solution, it contains 111 µL 30% 19:1 acrylamide-bis solution, 889 µL water, 0.8 µL TEMED, and 7.5 µL 10% APS. The polymerization time was determined by poking/lifting the gel. Depending on the curing time, a color was assigned for each concentration. 19:1 (FIG. 7C) and 29:1 (FIG. 7D) acrylamide-bis solution with TEMED and APS was added to a PLA device with a PLA bottom to determine how PLA affects polymerization time. 29:1 (FIG. 7E) acrylamide-bis solution with TEMED and APS was added to a PLA device that did not have a PLA bottom. The device was attached to a glass slide.
Figure 7D:
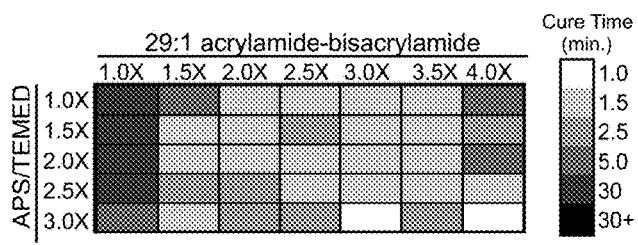
Figure 7E:
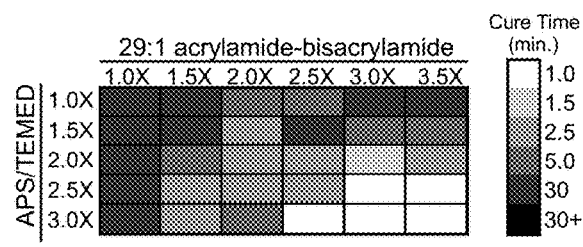

In order to determine if DNA was sheared during the course of the experiments, DNA was digested with HindIII, loaded, run on an agarose gel and imaged (SI Methods 1.3). In Lane-1, YOYO-1 DNA concentrated from the device and Lane-2 was a stock solution of YOYO-1 stained lambda DNA and both samples were digested with HindIII. If the recovered DNA were damaged during concentration, then the resulting bands in FIG. 5 would have smeared. The bands from the control and the sample were identical indicating DNA was full length after concentration at the roadblock. The slight mobility difference between lane-1 and lane-2 was the amount of YOYO-1 intercalated. Our concentrated sample did not have as much YOYO-1, which is why the mobility of the bands was faster [23] than the control and why lane-2 was brighter.

Example 9—Materials

Lambda dsDNA was purchased from New England Biolabs (Ipswich, Mass.). High gelling temperature agarose was purchased from Lonzo (Hayward, Calif.). 19:1 and 29:1 Bis-acrylamide was purchased from Bio-Rad (Hercules, Calif.). EDTA, Tris base, Fisher finest premium microscope slides, and 1 mM YOYO-1 (1,1-[1,3-propanediylbis[(dimethyliminio)-3,1-propanediyl] bis[4-[(3-methyl 2(3H)benzoxazolylidene)methyl]-quinolinium iodide) were purchased from ThermoFisher Scientific (Waltham, Mass.). Sodium hydroxide and sodium chloride were purchased from Sigma Aldrich (St Louis, Mo.). Ultimaker 2 was purchased from fbrc8 (Bartlett, Tenn.). Polylactic acid (PLA) filament and Ultimaker 3 printers were purchased from Dynamism (Chicago, Ill.). Sizzix double-sided adhesive sheets were purchased from Hobby Lobby (Kearney, Nebr.) and caulk (Alex Plus) was purchased from Wal-Mart (Kearney, Nebr.).

Example 10—Preparation of Gel Inserts

In order to make DNA inserts, A 0.5% high gelling temperature (HGT) agarose solution was prepared by boiling agarose in 1×TE buffer to make DNA inserts [1, 2]. Once the solution was clear, it was cooled ~42° C. before adding DNA. Lambda DNA (500 ng/μl) was added to the agarose solution and then pipetted into 3D printed PLA insert mold, with scotch tape on the bottom to create a well, (FIG. 12) and then placed on ice to solidify. For the qualitative experiments, DNA was added directly to agarose pored into the insert mold, so the exact concentration of DNA was known for each insert. The solidified inserts were popped out of the insert mold and placed into Eppendorf tubes with 200 μl 1×TE and stored at 4° C. DNA was stained with YOYO-1 the night before the experiment.

To make Kelcogel-agarose inserts, 0.75% Kelcogel LT100 and 0.25% HGT agarose are mixed and then heated until boiling. The mixture was cooled slightly and poured into the taped insert mold and allowed to harden and placed into 1×TE until ready to use. Sodium alginate-agarose inserts were made by mixing 0.50% agarose and 0.25% sodium alginate and boiled. The mixture was cooled and poured into the gel mold with CaCl$_2$ solution on the top and eventually bottom to make sure the alginate solidified.

Example 11—Analysis of Eluted DNA Using a Restriction Enzyme

A restriction enzyme assay was used to determine of the collected samples were full-length [3-5]. Concentration of the recovered DNA samples was determined using an Implan Nanophotometer P330. Each sample and control DNA (lambda) was digested with 20 units of HindIII in NEBuffer 2.1 and incubated at 37° C. (total volume: 30 µl) for 2-4 hrs. Following incubation, reactions were stopped with 2 µL of 0.5 M EDTA pH 8.0. Samples and control were loaded into a 0.5% HGT gel and run for 2 hrs at 65 V using a gel electrophoresis system (BioRad PowerPac Basic). The gel was stained with ethidium bromide and imaged utilizing a blue-light transilluminator and camera.

Example 12—Determine Overall Mobility of Bromophenol Blue in 29:1 Polyacrylamide Gel Similar to Lallman et al., the overall mobility of bromophenol blue was determined in 29:1 polyacrylamide gel in a dynamic range of ionic strength solutions using Ferguson plots [6]. For each solution (Ionic Strength=0.350, 0.782, 4.23, 8.38, and 16.1 mM), a series of TE solutions were diluted and used as the buffer for each experiment. To measure the ionic strength, the conductivity of each TE buffer was compared to a standard NaCl curve to determine the ionic strength. For the acrylamide gels at each ionic strength solution, the following gel concentrations were made (4.93%, 7.39%, 9.86%, and 12.30%) and they were poured into a 3D printed gel mold that was developed for Lallman et al. Once the gel was solidified, it was added to a gel box with the corresponding buffer and allowed to equilibrate for 1 hour. Loading dye (0.25% bromophenol blue, 0.25% xylene cyanol FF and 15% Ficoll; 2.5 µl) was added to a well, so the overall mobility of the dye could be tracked. Voltage (75 V) was applied to the gel box and run until there was noticeable separation between the dye and well. The overall mobility of the dye was calculated based on the distance, time, and the electric field.

Example 13—Concluding Remarks

A 3D printed mesofluidic device was developed with a polyacrylamide roadblock to concentrate DNA electrokinetically at the interface between a polyacrylamide roadblock and solution. 84% of DNA was eluted from DNA inserts in 1 hr. and recovered 45% of the eluted full-length lambda DNA. DNA eluted from this device can be used for Nanocoding or other sequencing platforms that require extremely large DNA for genome analysis. As DNA size increases, DNA mobility inside the acrylamide should decrease thus improving our ability to concentrate DNA molecules in solution.

[1] Genomes Project, C., Auton, A., Brooks, L. D., Durbin, R. M., Garrison, E. P., Kang, H. M., Korbel, J. O., Marchini, J. L., McCarthy, S., McVean, G. A., Abecasis, G. R., *Nature* 2015, 526, 68-74.

[2] Conrad, D. F., Pinto, D., Redon, R., Feuk, L., Gokcumen, O., Zhang, Y., Aerts, J., Andrews, T. D., Barnes, C., Campbell, P., Fitzgerald, T., Hu, M., Ihm, C. H., Kristiansson, K., Macarthur, D. G., Macdonald, J. R., Onyiah, I., Pang, A. W., Robson, S., Stirrups, K., Valsesia, A., Walter, K., Wei, J., Wellcome Trust Case Control, C., Tyler-Smith, C., Carter, N. P., Lee, C., Scherer, S. W., Hurles, M. E., *Nature* 2010, 464, 704-712.

[3] Chen, C., Qiao, R., Wei, R., Guo, Y., Ai, H., Ma, J., Ren, J., Huang, L., *BMC Genomics* 2012, 13, 733.

[4] Stefansson, H., Meyer-Lindenberg, A., Steinberg, S., Magnusdottir, B., Morgen, K., Arnarsdottir, S., Bjornsdottir, G., Walters, G. B., Jonsdottir, G. A., Doyle, O. M., Tost, H., Grimm, O., Kristjansdottir, S., Snorrason, H., Davidsdottir, S. R., Gudmundsson, L. J., Jonsson, G. F., Stefansdottir, B., Helgadottir, I., Haraldsson, M., Jonsdottir, B., Thygesen, J. H., Schwarz, A. J., Didriksen, M., Stensbol, T. B., Brammer, M., Kapur, S., Halldorsson, J. G., Hreidarsson, S., Saemundsen, E., Sigurdsson, E., Stefansson, K., *Nature* 2014, 505, 361-366.

[5] Wang, Y., Xiong, G., Hu, J., Jiang, L., Yu, H., Xu, J., Fang, Y., Zeng, L., Xu, E., Xu, J., Ye, W., Meng, X., Liu, R., Chen, H., Jing, Y., Wang, Y., Zhu, X., Li, J., Qian, Q., *Nat Genet* 2015, 47, 944-948.

[6] Freeman, J. L., Perry, G. H., Feuk, L., Redon, R., McCarroll, S. A., Altshuler, D. M., Aburatani, H., Jones, K. W., Tyler-Smith, C., Hurles, M. E., Carter, N. P., Scherer, S. W., Lee, C., *Genome Res* 2006, 16, 949-961.

[7] Teague, B., Waterman, M. S., Goldstein, S., Potamousis, K., Zhou, S., Reslewic, S., Sarkar, D., Valouev, A., Churas, C., Kidd, J. M., Kohn, S., Runnheim, R., Lamers, C., Forrest, D., Newton, M. A., Eichler, E. E., Kent-First, M., Surti, U., Livny, M., Schwartz, D. C., *Proc Natl Acad Sci USA* 2010, 107, 10848-10853.

[8] Gupta, A., Place, M., Goldstein, S., Sarkar, D., Zhou, S., Potamousis, K., Kim, J., Flanagan, C., Li, Y., Newton, M. A., Callander, N. S., Hematti, P., Bresnick, E. H., Ma, J., Asimakopoulos, F., Schwartz, D. C., *Proc Natl Acad Sci USA* 2015, 112, 7689-7694.

[9] Dimalanta, E. T., Lim, A., Runnheim, R., Lamers, C., Churas, C., Forrest, D. K., de Pablo, J. J., Graham, M. D., Coppersmith, S. N., Goldstein, S., Schwartz, D. C., *Anal Chem* 2004, 76, 5293-5301.

[10] Gupta, A., Kounovsky-Shafer, K. L., Ravindran, P., Schwartz, D., *Microfluidics and Nanofluidics* 2016, 20, 1-14.

[11] Jo, K., Schramm, T., Schwartz, D. C., in: Lee, J. (Ed.), *Micro and Nano Technologies in Bioanalysis*, Humana Press, Totowa 2009, pp. 29-42.

[12] Kounovsky-Shafer, K. L., Hernandez-Ortiz, J. P., Potamousis, K., Tsvid, G., Place, M., Ravindran, P., Jo, K., Zhou, S., Odijk, T., de Pablo, J. J., Schwartz, D. C., *Proc Natl Acad Sci USA* 2017, 114, 13400-13405.

[13] Kounovsky-Shafer, K. L., Hernandez-Ortiz, J. P., Jo, K., Odijk, T., de Pablo, J. J., Schwartz, D. C., *Macromolecules* 2013, 46, 8356-8368.

[14] Kim, Y., Kim, K. S., Kounovsky, K. L., Chang, R., Jung, G. Y., dePablo, J. J., Jo, K., Schwartz, D. C., *Lab Chip* 2011, 11, 1721-1729.

[15] Herschleb, J., Ananiev, G., Schwartz, D. C., *Nat Protoc* 2007, 2, 677-684.

[16] Schwartz, D. C., Cantor, C. R., *Cell* 1984, 37, 67-75.

[17] Garvin, A. M., Fritsch, A., *J Forensic Sci* 2013, 58 Suppl 1, S173-175.

[18] Hudlow, W. R., Krieger, R., Meusel, M., Sehhat, J. C., Timken, M. D., Buoncristiani, M. R., *Forensic Science Int Genet* 2011, 5, 226-230.

[19] Bordelon, H., Russ, P. K., Wright, D. w., Haselton, F. R., *PloS one* 2013, 8, e68369.

[20] Rueden, C. T., Schindelin, J., Hiner, M. C., DeZonia, B. E., Walter, A. E., Arena, E. T., Eliceiri, K. W., *BMC Bioinformatics* 2017, 18, 529.

[21] Stellwagen, N. C., *Electrophoresis* 2009, 30 Suppl 1, S188-195.
[22] Lallman, J., Flaugh, R., Kounovsky-Shafer, K. L., *Electrophoresis* 2018, 39, 862-868.
[23] Maschmann, A., Kounovsky-Shafer, K. L., *Nucleosides Nucleotides Nucleic Acids* 2017, 1-12.

What is claimed is:

1. A mesofluidic device for eluting and concentrating a plurality of nucleic acid molecules, the mesofluidic device comprising:
a device frame having a bottom surface upon which is defined a first reservoir comprising a first electrode, a second reservoir comprising a second electrode, the first and second electrodes configured for electrical connection, and an elongated channel extending between the first reservoir and the second reservoir, the elongated channel defined by a first wall opposing a second wall and having a channel width extending between an edge of the first wall to an edge of the second wall;
a first slot having a first slot width, the first slot configured to receive a gel insert comprising the plurality of nucleic acid molecules, wherein the first slot intersects the elongated channel across the channel width; and
a second slot having a second slot width, the second slot configured to receive a separation material having a first porosity, wherein the second slot intersects the elongated channel across the channel width,
wherein each of the first slot width and the second slot width is greater than the channel width, such that the first and second slots extend beyond the edges of the first and second walls, respectively, of the elongated channel, and
wherein at least a portion of the elongated channel extends between the second slot and the second reservoir.

2. The mesofluidic device of claim 1, wherein the plurality of nucleic acid molecules comprises deoxyribonucleic acid (DNA) molecules.

3. The mesofluidic device of claim 1, further comprising an electrical wire electrically connecting the first and second electrodes to a power supply.

4. The mesofluidic device of claim 1, wherein the separation material is a gel, a filter, or a physical barrier.

5. The mesofluidic device of claim 4, wherein the gel is a poly-acrylamide gel.

6. The mesofluidic device of claim 1, wherein the separation material has a pore size ranging from about 100 nanometers (nm) to about 200 nm.

7. The mesofluidic device of claim 1, wherein the separation material slows down or prevents a portion of the plurality of nucleic acid molecules from permeating or diffusing through.

8. The mesofluidic device of claim 1, wherein the nucleic acid molecules have a length ranging from about 45 kilobases (kb) to about 800 kb.

9. The mesofluidic device of claim 1, further comprising a third slot having a third slot width, wherein the third slot is configured to receive a separation material having a second porosity.

10. The mesofluidic device of claim 1, further comprising a fourth slot having a fourth slot width, wherein the fourth slot is configured to receive a separation material having a third porosity.

11. The mesofluidic device of claim 1, wherein the elongated channel is tapered.

12. A method of eluting and concentrating a plurality of nucleic acid molecules, the method comprising:
providing a mesofluidic device comprising:
a device frame having a bottom surface upon which is defined a first reservoir comprising a first electrode, a second reservoir comprising a second electrode, the first and second electrodes configured for electrical connection, and an elongated channel extending between the first reservoir and the second reservoir, the elongated channel defined by a first wall opposing a second wall and having a channel width extending between an edge of the first wall to an edge of the second wall;
a first slot having a first slot width, the first slot configured to receive a gel insert comprising the plurality of nucleic acid molecules, wherein the first slot intersects the elongated channel across the channel width; and
a second slot having a second slot width, the second slot configured to receive a separation material having a first porosity, wherein the second slot intersects the elongated channel across the channel width,
wherein each of the first slot width and the second slot width is greater than the channel width, such that the first and second slots extend beyond the edges of the first and second walls, respectively, of the elongated channel, and
wherein at least a portion of the elongated channel extends between the second slot and the second reservoir;
depositing the gel insert comprising the plurality of nucleic acid molecules in the first slot;
depositing the separation material in the second slot;
adding a buffer solution to the elongated channel;
applying an electrical voltage across the first and the second electrodes;
eluting the plurality of nucleic acid molecules from the gel insert; and
concentrating the plurality of nucleic acid molecules at a concentration region disposed between the first slot and the second slot.

13. The method of claim 12, wherein placing the separation material comprises:
inserting a first piece of polydimethylsiloxane (PDMS) at a first end of the second slot;
inserting a second piece of PDMS at a second end of the second slot;
adding acrylamide, bis-acrylamide, and an initiator between the first piece and the second piece of PDMS; and
removing the first and second pieces of PDMS after polymerization of the separation material occurs.

14. The method of claim 13, wherein the separation material has a concentration of acrylamide and bis-acrylamide that is twice as much as the concentration of an initiator.

15. The method of claim 12, wherein the electrical voltage is between about 10 V and 30 V.

16. The method of claim 12, wherein about 75% to 90% of the plurality of nucleic acid molecules is eluted from the gel insert.

17. The method of claim 12, wherein about 35% to 75% of the plurality of nucleic acid molecules is collected at the concentration region.

18. The method of claim 12, wherein the separation material has a pore size ranging from about 100 nanometers (nm) to about 200 nm.

19. The method of claim 12, wherein the separation material slows down or prevents a portion of the plurality of nucleic acid molecules from permeating or diffusing through.

20. The method of claim 12, wherein the nucleic acid molecules have a length ranging from about 45 kilobases (kb) to about 800 kb.

\* \* \* \* \*

UNITED STATES PATENT AND TRADEMARK OFFICE
CERTIFICATE OF CORRECTION

| | | |
|---|---|---|
| PATENT NO. | : 11,668,631 B2 | Page 1 of 1 |
| APPLICATION NO. | : 16/592695 | |
| DATED | : June 6, 2023 | |
| INVENTOR(S) | : Kristy Leigh Kounovsky-Shafer et al. | |

It is certified that error appears in the above-identified patent and that said Letters Patent is hereby corrected as shown below:

On the Title Page

Item [71] please delete "Board of Regents of the University of Nebraska, Lincoln, NE (US)" and insert therefore -- NUtech Ventures, Lincoln, NE (US) --.

Signed and Sealed this
Fifteenth Day of April, 2025

Coke Morgan Stewart
*Acting Director of the United States Patent and Trademark Office*